United States Patent
Wang et al.

(10) Patent No.: US 7,470,795 B2
(45) Date of Patent: Dec. 30, 2008

(54) SYNTHESIS OF 6,7-DIHYDRO-5H-IMIDAZO[1,2-A] IMIDAZOLE-3-SULFONIC ACID AMIDES

(75) Inventors: Xiao-jun Wang, Danbury, CT (US); Thomas Wirth, Stadecken-Elsheim (DE); Thomas Nicola, Ingelheim (DE); Li Zhang, New Milford, CT (US); Rogelio Perez Frutos, Sandy Hook, CT (US); Yibo Xu, New Milford, CT (US); Dhileepkumar Krishnamurthy, Brookfield, CT (US); Laurence John Nummy, Newburgh, NY (US); Richard J. Varsolona, Scotch Plains, NJ (US); Chris Hugh Senanayake, Brookfield, CT (US); Jutta Kroeber, Bingen-Dietersheim (DE); Diana Reeves, New Milford, CT (US)

(73) Assignees: Boehringer Ingelheim Pharmaceuticals, Inc., Ridgefield, CT (US); Boehringer Ingelheim International GmbH, Ingelheim (DE)

( * ) Notice: Subject to any disclaimer, the term of this patent is extended or adjusted under 35 U.S.C. 154(b) by 539 days.

(21) Appl. No.: 11/188,377

(22) Filed: Jul. 25, 2005

(65) Prior Publication Data

US 2006/0025447 A1    Feb. 2, 2006

Related U.S. Application Data

(60) Provisional application No. 60/591,398, filed on Jul. 27, 2004.

(51) Int. Cl.
*C07D 235/00* (2006.01)

(52) U.S. Cl. .............. 548/303.1; 548/300.1; 548/301.7; 548/302.7; 544/106; 544/111; 544/132; 544/358

(58) Field of Classification Search .............. 548/300.1, 548/301.7, 302.7, 303.1; 544/106, 111, 132, 544/358
See application file for complete search history.

(56) References Cited

U.S. PATENT DOCUMENTS

| | | | |
|---|---|---|---|
| 6,414,161 B1 * | 7/2002 | Frutos et al. ............. | 548/303.1 |
| 6,458,986 B1 * | 10/2002 | Frutos et al. ................. | 560/34 |
| 6,492,408 B1 * | 12/2002 | Wu et al. ..................... | 514/387 |
| 6,844,360 B2 * | 1/2005 | Kelly et al. ................. | 514/387 |
| 6,852,748 B1 * | 2/2005 | Kelly et al. ................. | 514/387 |
| 2002/0028949 A1 | 3/2002 | Frutos et al. | |

| | | | |
|---|---|---|---|
| 2006/0025447 A1 | 2/2006 | Wang et al. | |

FOREIGN PATENT DOCUMENTS

| | | |
|---|---|---|
| WO | WO 01/07440 A1 | 2/2001 |
| WO | WO 2004/041273 A1 | 5/2004 |
| WO | WO 2004/041827 A2 | 5/2004 |
| WO | 2006014828 A1 | 2/2006 |

OTHER PUBLICATIONS

Wu, J.P., et al., "Second-Generation Lymphocyte Function-Associated Antigen-1 Inhibitors: 1H-Imidazo [1,2-alpha]imidazol-2-one Derivatives", J. Med. Chem. 2004, vol. 47, pp. 5356-5366.
Frutos et al.; An improved synthesis of N-aryl-hydantoin LFA-1 antagonists via the enantiospecific alkylation of an isobutyraldehyde-derived imidazolidinone template; Tetrahedron: Asymmetry; 2001; vol. 12; pp. 101-104.
Yee; Self-Regeneration of Stereocenters: A Practicle Enantiospecific Synthesis of LFA-1 Antagonists BIRT-377; Organic Letters; 2000; vol. 2; No. 18; pp. 2781-2783.
Thavonekham; A Practicle Synthesis of Ureas from Phenyl Carbamates; Synthesis; Oct. 1997; pp. 1189-1194.
International Search Report (Form PCT/ISA/220) for PCT/US2007/060552.

* cited by examiner

*Primary Examiner*—Golam M Shameem
(74) *Attorney, Agent, or Firm*—Michael P. Morris; Mary-Ellen M. Devlin; Philip I. Datlow

(57) ABSTRACT

Disclosed is a multi-step process for preparing a compound of Formula I:

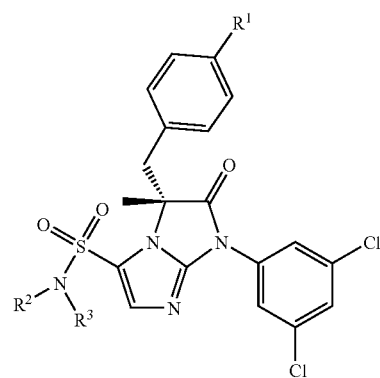

wherein $R^1$ to $R^3$ are as defined herein. The compounds of formula I inhibit the binding of human intercellular adhesion molecules to the Leukointegrins. As a result, these compounds are useful in the treatment of inflammatory and immune cell-mediated diseases.

4 Claims, No Drawings

SYNTHESIS OF 6,7-DIHYDRO-5H-IMIDAZO[1,2-A] IMIDAZOLE-3-SULFONIC ACID AMIDES

This application claims benefit to U.S. Provisional Application No. 60/591,398, filed Jul. 27, 2004.

TECHNICAL FIELD

The invention relates to an improved process for the preparation of 6,7-dihydro-5H-imidazo[1,2-a]imidazole-3-sulfonic acid amides useful as agents for the treatment of inflammatory and immune-cell mediated diseases.

BACKGROUND OF THE INVENTION 6,7-Dihydro-5H-imidazo[1,2-a]imidazole-3-sulfonic acid amides of formula I below, wherein $R^1$ to $R^3$ are as defined herein, have been reported as small molecule inhibitors of the binding of human intercellular adhesion molecules, including ICAM-1, ICAM-2 and ICAM-3, to the Leukointegrins, especially CD18/CD11a. As a result, these small molecules are useful in the treatment of inflammatory and immune cell-mediated diseases (See U.S. Pat. No. 6,492,408, U.S. Pat. No. 6,844,360, WO 2004/041827 A2, U.S. Pat. No. 6,852,748, and WO 2004/041273 A1).

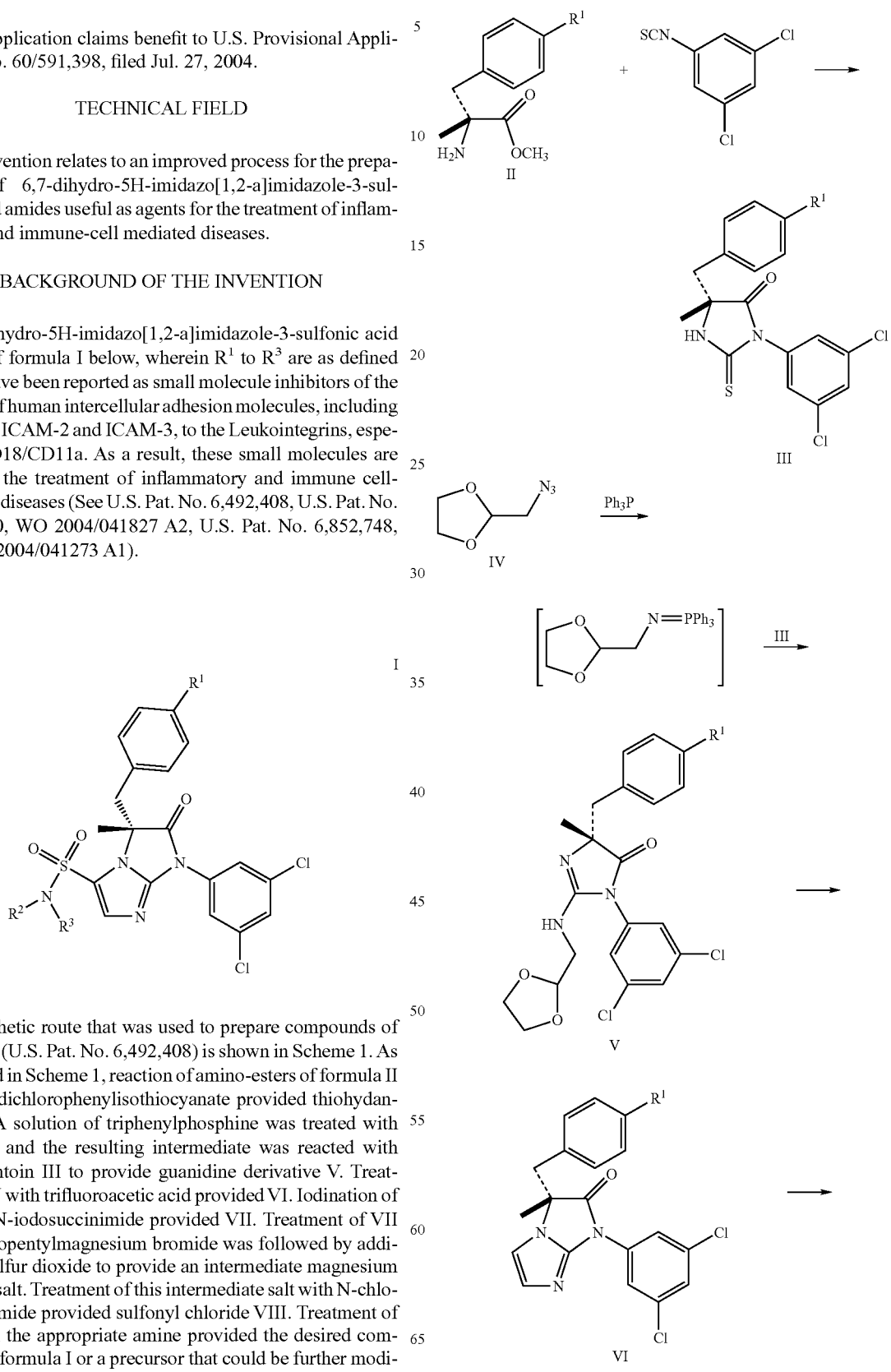

A synthetic route that was used to prepare compounds of formula I (U.S. Pat. No. 6,492,408) is shown in Scheme 1. As illustrated in Scheme 1, reaction of amino-esters of formula II with 3,5-dichlorophenylisothiocyanate provided thiohydantoin III. A solution of triphenylphosphine was treated with azide IV, and the resulting intermediate was reacted with thiohydantoin III to provide guanidine derivative V. Treatment of V with trifluoroacetic acid provided VI. Iodination of VI with N-iodosuccinimide provided VII. Treatment of VII with cyclopentylmagnesium bromide was followed by addition of sulfur dioxide to provide an intermediate magnesium sulfinate salt. Treatment of this intermediate salt with N-chlorosuccinimide provided sulfonyl chloride VIII. Treatment of VIII with the appropriate amine provided the desired compound of formula I or a precursor that could be further modified to provide the desired compound.

-continued
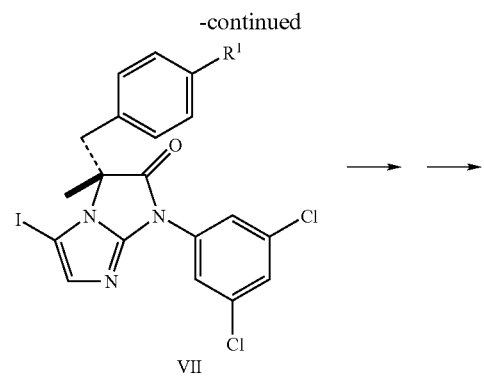
VII
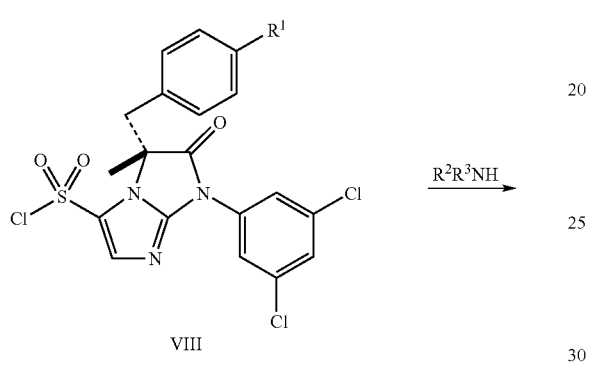
VIII
R²R³NH →
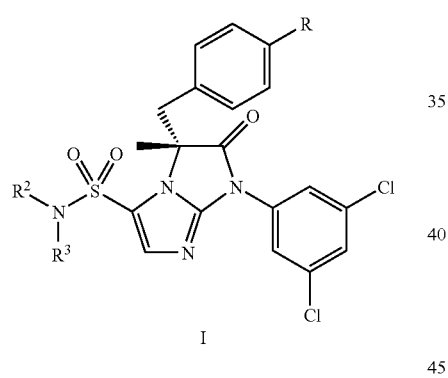
I
An alternate synthesis of intermediate VII illustrated in Scheme 2 was described in U.S. Pat. No. 6,414,161:
Scheme 2
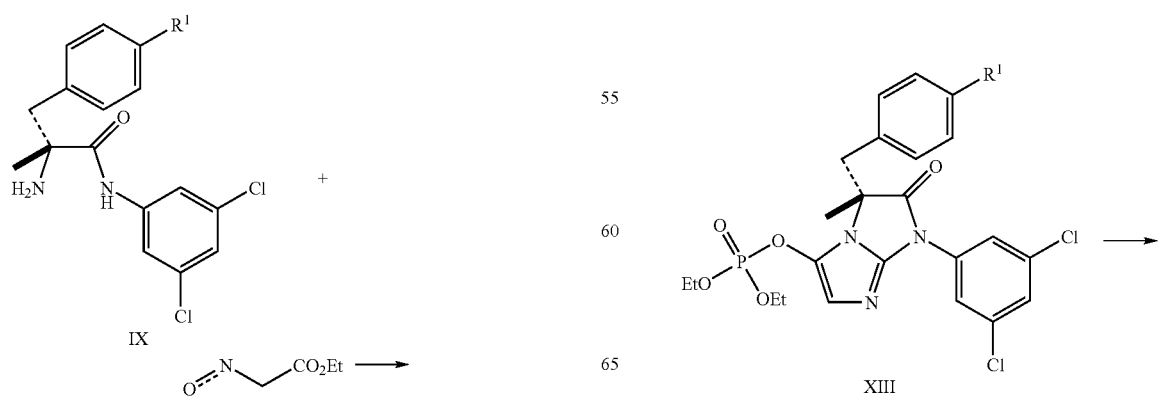
-continued
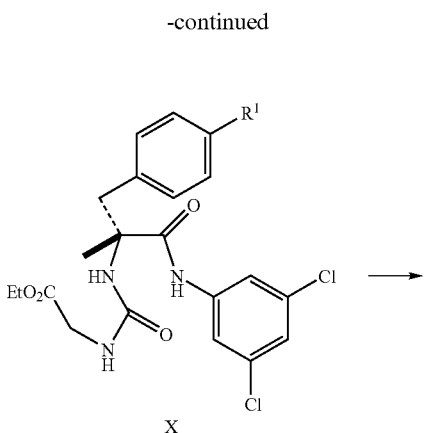
X
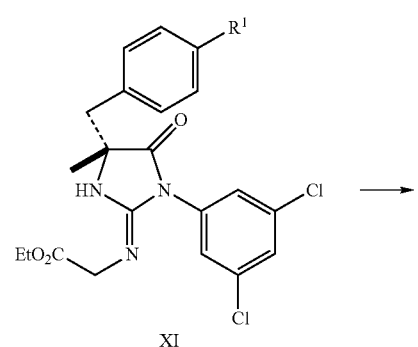
XI
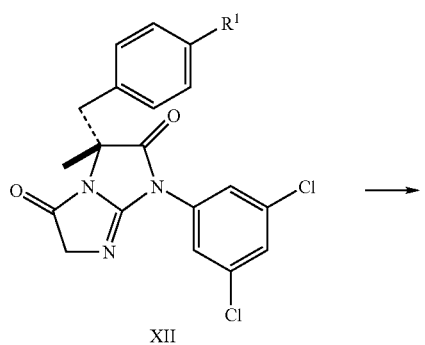
XII
XIII -continued

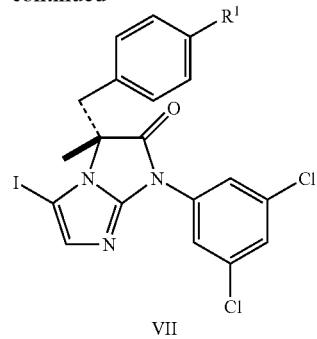

VII

As illustrated in Scheme 2, reaction of amino-amide IX with ethyl isocyanatoacetate provided urea X. Dehydration-cyclization of X with carbon tetrachloride, triphenylphosphine and triethylamine produced guanidine XI. Treatment of XI with trimethylaluminum provided lactam XII. Reaction of lactam XII with ethyl chlorophosphate and bis(trimethylsilyl) amide provided phosphate XIII. Iodination of XIII with trimethylsilyl chloride and sodium iodide provided iodo intermediate VII.

Disadvantages of the above two procedures include the use of potentially hazardous reagents such as azide IV (Scheme 1) and the requirement of chromatographic purification, such as purification of XII (Scheme 2). Therefore, the synthetic methods outlined above are not suitable for large scale preparation of compounds of formula I.

SUMMARY OF THE INVENTION

The present invention is directed to a novel process for the preparation of compounds of formula I. This process is practical and economical, involves fewer chemical steps and no chromatographic purification. One aspect of the invention is directed to a novel process for preparing compounds of formula I:

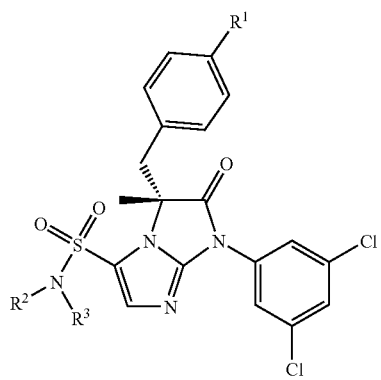

I wherein $R^1$ is selected from bromo, trifluoromethoxy, cyano and pyrimidin-5-yl optionally mono- or di-subsituted by $NH_2$; and
$R^2$ and $R^3$ are each independently selected from the group consisting of
(A) hydrogen; and
(B) a $C_{1-4}$ straight or branched alkyl group, optionally mono- or disubstituted with moieties independently selected from oxo, —OH, $NH_2$ and —C(O)$NR^4R^5$, where $R^4$ and $R^5$ are independently selected from:
(1) hydrogen, and
(2) a $C_{1-4}$ straight or branched alkyl group which alkyl group is mono- or disubstituted with moieties independently selected from $CONH_2$ and OH; or $R^2$ and $R^3$, combined with the nitrogen they are bonded to, form:
(1) a pyrrolidine or piperidine ring, each optionally substituted with the group —C(O)$NR^6R^7$, where $R^6$ and $R^7$ are independently selected from
(A) hydrogen; and
(B) a $C_{1-4}$ straight or branched alkyl group, optionally mono- or disubstituted with moieties independently selected from oxo, —OH and $NH_2$;
(2) a morpholine ring; or
(3) a piperazine ring;

or a pharmaceutically acceptable salt thereof.

The process comprises the following steps (wherein, unless otherwise defined, all the substituent groups in the chemical formulas depicted in the synthetic steps hereafter have the same definitions as set forth above for formula I):

a) reacting a compound of the formula XIV and a compound of the formula XV in the presence of a strong base at a temperature from 0° C. to ambient temperature, in an aprotic organic solvent, to provide a compound of the formula XVI.

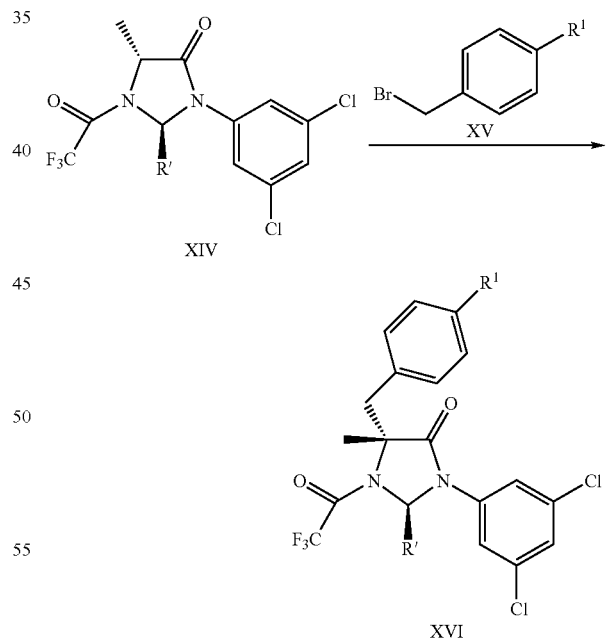

R' = t-Bu or i-Pr b) deprotecting and hydrolyzing a compound of formula XVI produced in step a) by treating the compound of formula XVI with a phase transfer catalyst and a base in tetrahydrofuran or 2-methyl tetrahydrofuran, followed by an acid to form a compound of formula XVII:

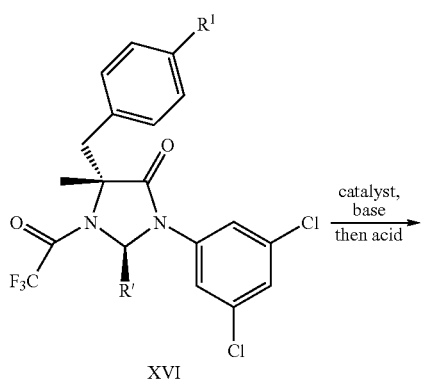

XVI

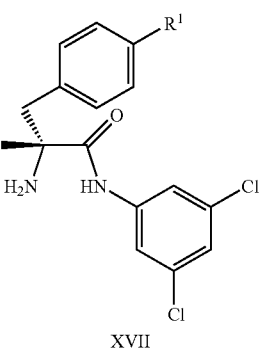

XVII c) reacting the compound of formula XVII produced in step b) with a compound of formula XVIII where $R^a$ is aryl and $R^b$ is $C_{1-4}$ alkyl, and an organic base in a polar organic solvent to form a compound of the formula XIX.

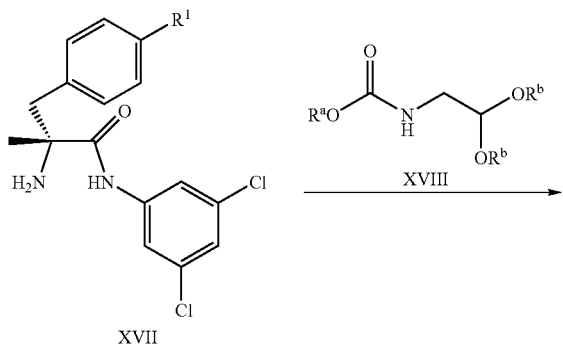

XVII     XVIII

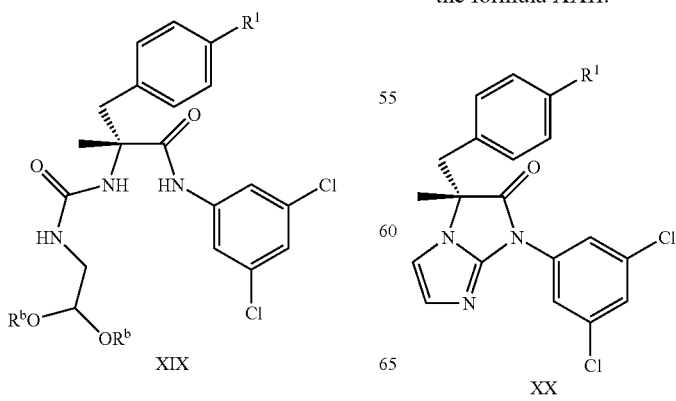

XIX d) reacting the compound of formula XIX produced in step c) with a compound of formula $(R^c)_3P$, where $R^c$ is $C_{1-4}$alkyl, $C_{3-6}$cycloalkyl or aryl, a carbon tetrahalide and a tri-$C_{1-6}$alkylamine in an aprotic organic solvent, followed by adding an acid to form a compound of the formula XX, or d) alternatively, reacting a compound of the formula XIX produced in step c) with a compound of the formula $(R^c)_3PX_2$, wherein $R^c$ is $C_{1-4}$alkyl, $C_{3-6}$cycloalkyl or aryl, and X is a halide, and a tri-$C_{1-6}$alkylamine, in an aprotic organic solvent, followed by adding an acid to form a compound of the formula XX, or d) alternatively, reacting a compound of formula XIX produced in step c) with a boronic acid compound $ArB(OH)_2$, wherein Ar is an aromatic carbocyclic group substituted with one or more electron withdrawing groups, in an aprotic organic solvent to form a compound of the formula XX:

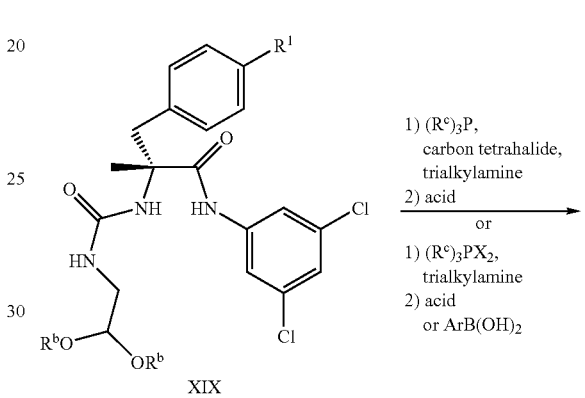

XIX

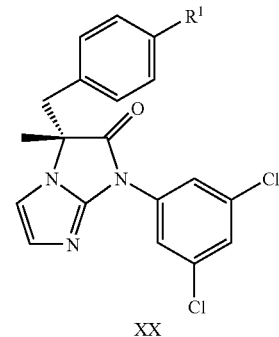

XX e) reacting the compound of the formula XX produced in step d) with a compound of the formula XXI, where Y is a halogen, in a aprotic organic solvent to form a compound of the formula XXII:

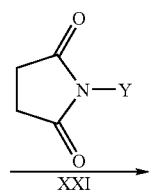

XX     XXI

-continued

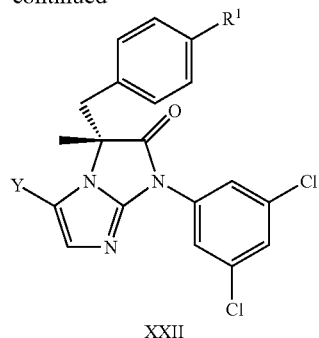

XXII f) reacting the compound of formula XXII produced in step e) with a compound of formula $R^dMgY$, where $R^d$ is $C_{1-6}$ alkyl or $C_{3-6}$ cycloalkyl and Y is halogen, sulfur dioxide and N-chlorosuccinimide, followed by a base and a compound of the formula XXIII in an aprotic organic solvent to form a compound of the formula I, without isolation of intermediates formed during this step.

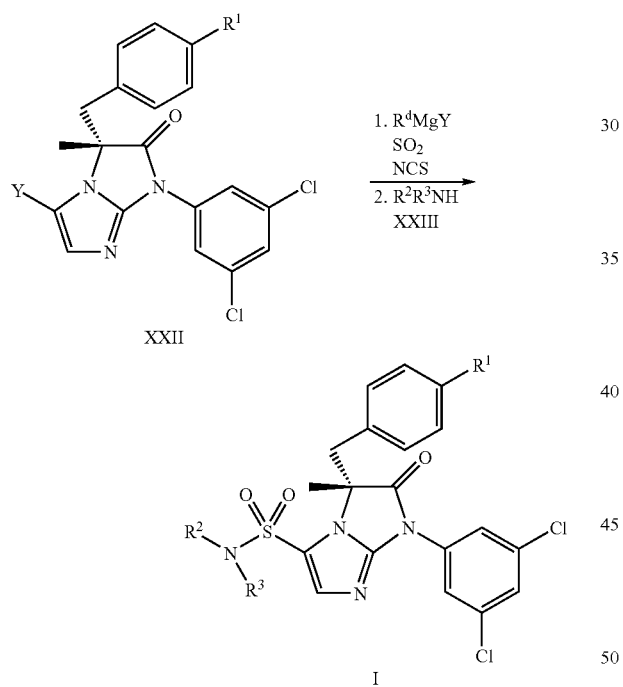

The final compounds of formula I can be converted to its pharmaceutically acceptable salts using any conventional techniques known in the art.

DETAILED DESCRIPTION OF THE INVENTION

Terms not specifically defined herein should be given the meanings that would be given to them by one of skill in the art in light of the disclosure and the context.

In general, all tautomeric forms and isomeric forms and mixtures, whether individual geometric isomers or optical isomers or racemic or non-racemic mixtures of isomers, of a chemical structure or compound are intended, unless the specific stereochemistry or isomeric form is specifically indicated in the compound name or structure.

The individual steps of the inventive process are described in detail below, along with other aspects of the present invention. The present invention includes not only the described multi-step process, but also the individual steps of the multi-step process and the various novel intermediates that are formed or used in such process steps.

Optimum reaction conditions and reaction times for each individual step may vary depending on the particular reactants employed. Unless otherwise specified, solvents, temperatures and other reaction conditions may be readily selected by one of ordinary skill in the art. Specific procedures are provided in the Synthetic Examples section. Typically, reaction progress may be monitored by high pressure liquid chromatography (HPLC) if desired. Intermediates and products may be purified by crystallization. Unless otherwise described, the starting materials and reagents are either commercially available or may be prepared by one skilled in the art from commercially available materials using methods described in the chemical literature.

Step (a)

The starting materials of formula XIV used in this first step are prepared as described by N. Yee, Org. Lett. 2000, 2, 2781-2783, and R. Frutos, Tetrahedron: Asymmetry 2001, 12, 101-104, which are herein incorporated by reference in their entirety. This process is illustrated in Scheme 3.

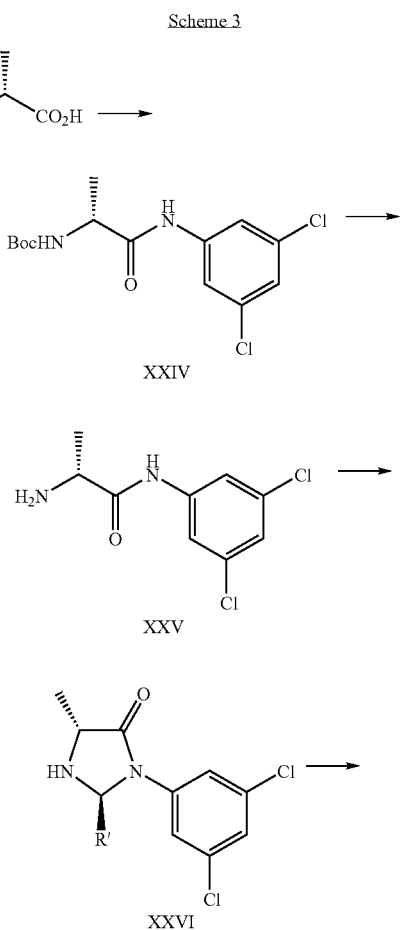

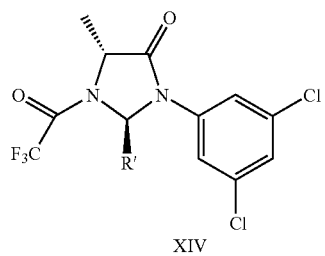

XIV

R' = t-Bu or i-Pr

Commercially available D-N-Boc-alanine was reacted with isobutyl chloroformate in the presence of N-methylmorpholine (−10° C., THF), followed by addition of 3,5-dichloroaniline to give amide XXIV. Deprotection of the crude N-Boc-alaninamide by treatment with TFA in dichloromethane produced amino amide XXV in 92% yield over two steps. The amino amide was reacted with pivalaldehyde or isobutyraldehyde in refluxing pentane, and the product XXVI was crystallized from the reaction mixture as a single diastereoisomer in >74% yield. Treatment of XXVI with trifluoroacetic anhydride, in methylene chloride, in presence of triethylamine yielded XIV in 98% yield.

In step (a) of the process of the present invention comprises reacting a compound of the formula XIV and a compound of the formula XV in the presence of a strong base at a temperature from 0° C. to ambient temperature, in an aprotic organic solvent, to provide a compound of the formula XVI.

A similar process step is described by N. Yee, *Org. Lett.* 2000, 2, 2781-2783; R. Frutos, *Tetrahedron: Asymmetry* 2001, 12, 101-104; U.S. Pat. No. 6,844,360, WO 2004/041827 A2, U.S. Pat. No. 6,852,748 and WO 2004/041273 A1.

Process step (a) of the present invention is improved by performing the reaction from 0° C. to ambient temperature as compared to −30 to 0° C. in the cited references. Examples of novel compounds of formula XVI (a, b, c, d and e) prepared using this improved process are illustrated below:

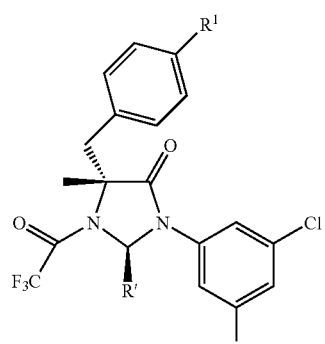

XIVa: R' = t-Bu, R¹ = Br
XIVb: R' = t-Bu, R¹ = CN
XIVc: R' = t-Bu, R¹ = OCF₃
XIVd: R' = t-Bu, R¹ = 5-pyrimidyl
XIVe: R' = i-Pr, R¹ = OCF₃

Step a) is performed in an aprotic organic solvent such as THF, ether or dimethoxyethane. Suitable bases include potassium tert-butoxide, lithium diisopropylamide, lithium bis(trimethylsilyl)amide, potassium bis(trimethylsilyl)amide and sodium bis(trimethylsilyl)amide.

Step (b)

Step (b) of the inventive process comprises deprotection of compounds of the formulas XVI. One may accomplish this with a base, optionally in the presence of a phase transfer catalyst such as trimethylbenzylammonium hydroxide, in a suitable solvent such as tetrahydrofuran, 2-methyl tetrahydrofuran or 2-propanol followed by treatment with an acid to form the corresponding amino amide of formulas XVII. Specific examples are illustrated below:

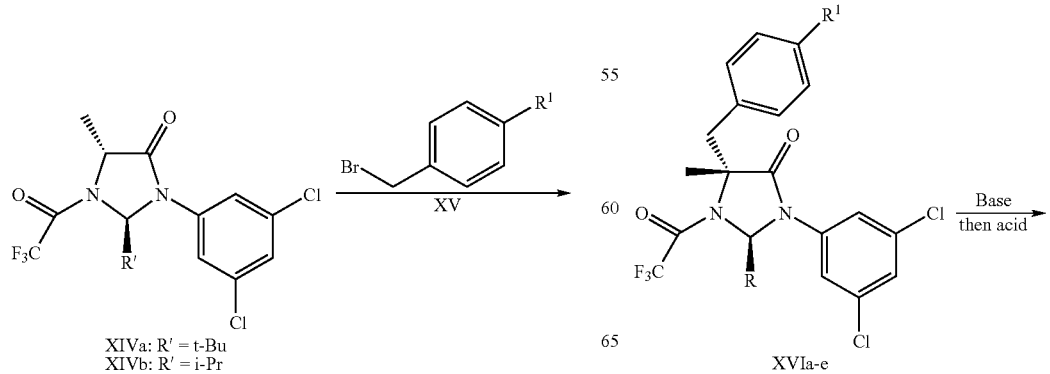

XIVa: R' = t-Bu
XIVb: R' = i-Pr

XVIa-e

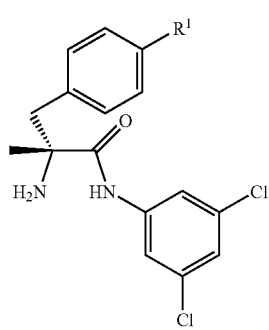

XVIIa: $R^1$ = Br
XVIIb: $R^1$ = CN
XVIIc: $R^1$ = $OCF_3$
XVIId: $R^1$ = 5-pyrimidyl A similar process step is described by N. Yee, *Org. Lett.* 2000, 2, 2781-2783; R. Frutos, *Tetrahedron: Asymmetry* 2001, 12, 101-104; U.S. Pat. No. 6,844,360, WO 2004/041827 A2, U.S. Pat. No. 6,852,748, and WO 2004/041273 A1.

Suitable bases for this step include alkali metal hydroxides such as sodium hydroxide or potassium hydroxide. Suitable acids include $H_2SO_4$ and HCl. Most preferred is potassium hydroxide in isopropyl alcohol followed by 3 M $H_2SO_4$. The novel compounds of the formulas XVIIa to XVIId produced in this step are another aspect of the present invention.

Step (c)

Step (c) of the inventive process comprises reacting a compound of the formula XVII produced in step b) with a compound of the formula XVIII, where $R^a$ is aryl and $R^b$ is $C_{1-4}$ alkyl, and an organic base in a polar organic solvent to form a compound of the formula XIX, in excellent yield. Specific examples are shown below.

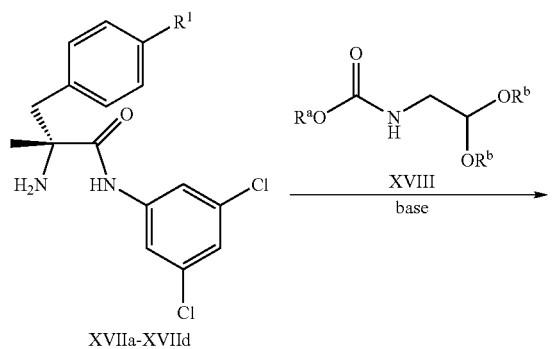

XVIIa-XVIId

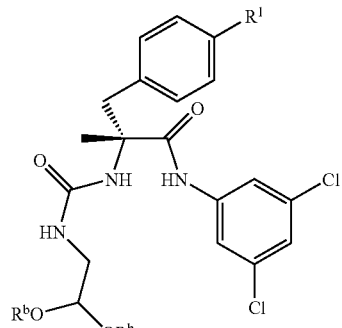

XIXa: $R^1$ = Br
XIXb: $R^1$ = CN
XIXc: $R^1$ = $OCF_3$
XIXd: $R^1$ = 5-pyrimidyl The formation of ureas by reaction of an amine with a phenyl carbamate is documented in the scientific literature (see for example, B. Thavonekham *Synthesis*, 1997, 1189-1194). The novel compounds of the formulas XIXa to XIXd produced in this step are another aspect of the present invention.

Suitable $C_{1-4}$ alkyl $R^b$ groups for the carbamate XVIII in step (c) include, for example, methyl, ethyl and cyclobutyl.

Step (c) is performed in a polar organic solvent, such as dimethylsulfoxide. Suitable organic bases include, for example, triethylamine, diisopropylethylamine and N-methylmorpholine.

Step (d)

Step (d) of the inventive process comprises reacting a compound of the formula XIX produced in step c) with a compound of the formula $(R^c)_3P$, where $R^c$ is $C_{1-4}$ alkyl, $C_{3-6}$ cycloalkyl or aryl, a carbon tetrahalide and a tri-$C_{1-6}$ alkylamine in an aprotic organic solvent, followed by adding an acid to form a compound of the formula XX, in excellent yield. Alternatively, reacting a compound of the formula XIX produced in step c) with a compound of the formula $(R^c)_3PX_2$, where $R^c$ is $C_{1-4}$ alkyl, $C_{3-6}$ cycloalkyl or aryl, X is a halide, and a tri-$C_{1-6}$ alkylamine in an aprotic organic solvent, followed by adding an acid provides a compound of the formula XX. Another alternative is to react a compound of formula XIX produced in step c) with a boronic acid compound $ArB(OH)_2$, wherein Ar is an aromatic carbocyclic group substituted with one or more electron withdrawing groups, in an aprotic organic solvent to form a compound of the formula XX. Specific examples are shown below.

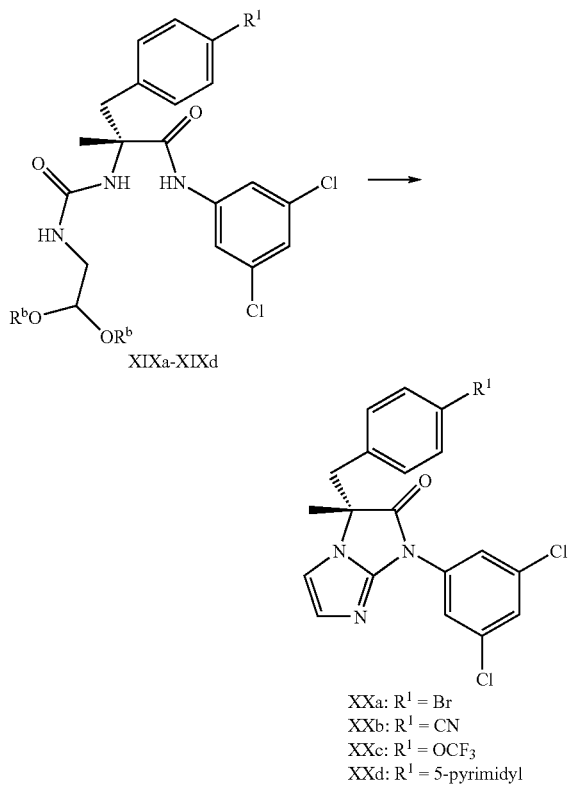

XIXa-XIXd

XXa: R$^1$ = Br
XXb: R$^1$ = CN
XXc: R$^1$ = OCF$_3$
XXd: R$^1$ = 5-pyrimidyl

The dehydration of a urea and subsequent cyclization to a guanidine derivative is described in Frutos et al., U.S. Pat. No. 6,414,161. However, in contrast to the procedure described in Frutos et al., in the process of the present invention the intermediate guanidine derivatives are not isolated and undergo a spontaneous cyclization to give the final bicyclic products of formula XX. Furthermore, use of the reagents (R$^c$)$_3$PX$_2$, for the dehydration/cyclization step is not described in Frutos et al.

Novel compounds of formulas XXa to XXd set forth above are another aspect of the present invention.

A preferred carbon tetrahalide to use in this step is carbon tetrachloride and a preferred tri-C$_{1-6}$alkylamine is triethylamine.

Step (d) is performed in an aprotic organic solvent. Suitable aprotic solvents for performing step (d) when reacting XIX with (R$^c$)$_3$P or (R$^c$)$_3$PX$_2$ include, for example, dichloromethane and acetonitrile. Examples of suitable (R$^c$)$_3$P in step (d) include trimethylphosphine, triethylphosphine and triphenylphosphine. Suitable carbon tetrahalides in step (d) include, for example, carbon tetrachloride, and carbon tetrabromide. Examples of suitable (R$^c$)$_3$PX$_2$ in step (d) include triphenylphosphine dichloride and triphenylphosphine dibromide. Examples of suitable acids in step (d) include hydrochloric acid and 4-toluenesulfonic acid.

Examples of suitable boronic acid compounds that may be employed for this conversion are compounds of the formula ArB(OH)$_2$, wherein Ar is an aromatic carbocyclic group, such as a phenyl or naphthyl group, substituted with one or more electron withdrawing groups, such as haloalkyl, halogen and nitro. Specific examples that may be mentioned are the compounds 3a to 3d below:

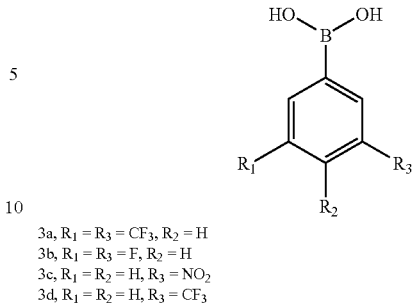

3a, R$_1$ = R$_3$ = CF$_3$, R$_2$ = H
3b, R$_1$ = R$_3$ = F, R$_2$ = H
3c, R$_1$ = R$_2$ = H, R$_3$ = NO$_2$
3d, R$_1$ = R$_2$ = H, R$_3$ = CF$_3$

Suitable organic solvents for performing step (d) when reacting XIX with the boronic acid compound include relatively high boiling point organic solvents, such as toluene, xylenes and isobutyl acetate.

Step (e)

Step (e) of the inventive process is a halogenation step that comprises reacting a compound of the formula XX produced in step d) with a compound of the formula XXI where Y is halide, in an aprotic organic solvent to form a compound of the formula XXII. Specific examples, where R$^1$ is trifluoromethoxy and 5-pyrimidyl are shown below:

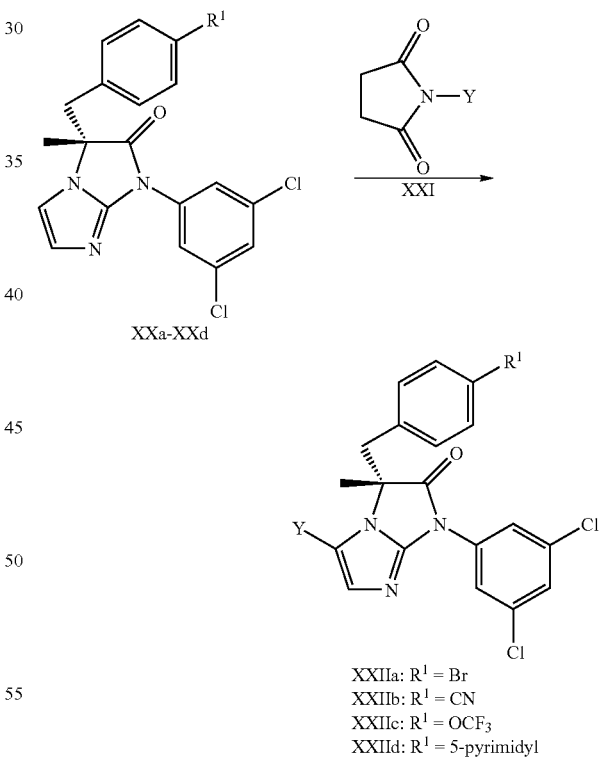

XXa-XXd

XXIIa: R$^1$ = Br
XXIIb: R$^1$ = CN
XXIIc: R$^1$ = OCF$_3$
XXIId: R$^1$ = 5-pyrimidyl This type of halogenation step is described in U.S. Pat. No. 6,492,408, and in U.S. Pat. No. 6,844,360, WO 2004/041827 A2, U.S. Pat. No. 6,852,748 and WO 2004/041273 A1.

In one embodiment of the present invention, the Y group in halogenated compounds of formula XXII is bromo and iodo. In a preferred embodiment, Y is bromo.

If iodination is conducted in Step (e), it is done in the presence of a Lewis acid such as pyridinium p-toluenesulfonate. We have found that bromination in step (e), proceeds most cleanly and in greatest yield if the reaction is run in the presence of a base such as triethyl amine, potassium carbonate, N,N-diisopropylethylamine, cesium carbonate, sodium carbonate or sodium phosphate, and preferably in dimethoxyethane or isopropyl acetate.

Step (e) is performed in an aprotic organic solvent. Suitable aprotic organic solvents include, for example, dichloromethane, acetone, ethylene glycol dimethyl ether, and diglyme.

Step (e) can be performed at a wide range of reaction temperatures, but preferably in the range of about −20° C. to about 60° C., more preferably at about −10° C. to about 40° C., more preferably about −5° C. to about 30° C., more preferably about 0° C. to about 25° C.

Step (f)

Step (f) of the inventive process comprises reacting of a compound of the formula XXII produced in step e) with a compound of the formula $R^d MgY$, where $R^d$ is $C_{1-6}$ alkyl or $C_{3-6}$cycloalkyl, and Y is halide, sulfur dioxide and N-chlorosuccinimide followed by a base and a compound of the formula XXIII in an aprotic organic solvent, to form a compound of the formula I without isolation of intermediates formed during this step. Specific examples are illustrated below.

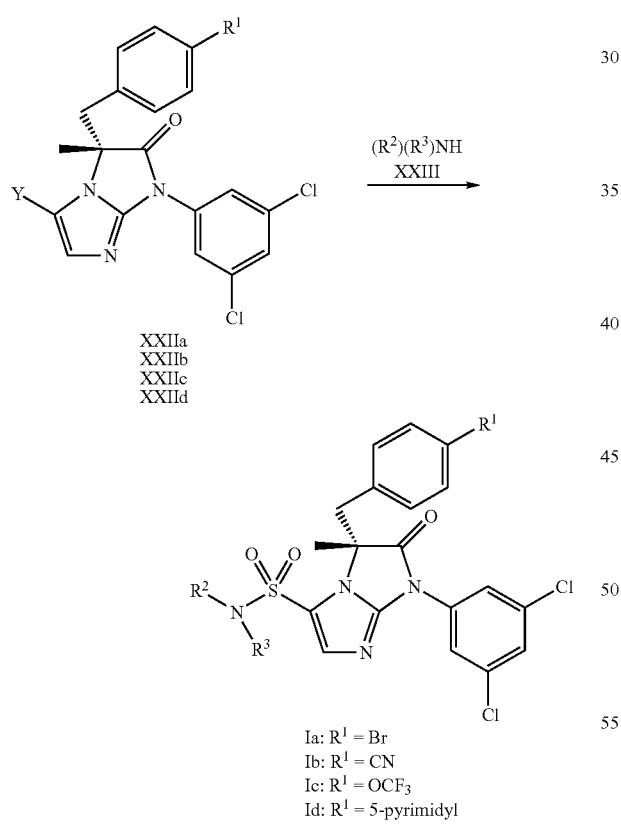

XXIIa
XXIIb
XXIIc
XXIId

Ia: $R^1$ = Br
Ib: $R^1$ = CN
Ic: $R^1$ = OCF$_3$
Id: $R^1$ = 5-pyrimidyl

A similar process step is described in U.S. Pat. No. 6,492,408, U.S. Pat. No. 6,844,360, WO 2004/041827 A2, U.S. Pat. No. 6,852,748 and WO 2004/041273 A1. In the present invention, however this process step is performed without isolation of any of the intermediates produced during the process. This one-pot process is not disclosed in the above cited reference.

Suitable $R^d MgY$ in step (f) include, for example, isopropylmagnesium chloride, isopropylmagnesium bromide, cyclopentylmagnesium chloride and cyclopentylmagnesium bromide.

When the $R^1$ group is 5-pyrimidyl (XXIId, for example) it is necessary to pre-mix an organic base such as N,N,N',N'-tetramethylethylene diamine, bis[2-(N,N-dimethylamino)ethyl] ether and N,N,N',N',N''-pentamethyldiethylenetriamine with $R^d MgY$, prior to reacting with the compound of formula XXIId. This will prevent addition of $R^d MgY$ to the 5-pyrimidyl group. This novel process is another aspect of the present invention and is not disclosed in the scientific literature.

Step (f) is carried out in an aprotic organic solvent, preferably tetrahydrofuran.

Suitable bases for use in step (f) include, for example, triethylamine, diisopropylethylamine, potassium carbonate, cesium carbonate and sodium carbonate.

The addition of $R^d MgY$ in step (f) is performed at a temperature of about −40° C. to about −15° C., preferably about −25° C. to about −15° C. The addition of sulfur dioxide and N-chlorosuccinimide is conducted at a temperature of about −40° C. to about −5° C., preferably about −15° C. to about −5° C. Addition of XXIII is performed at room temperature.

The addition XXIII is preferably carried out in the presence of water as a co-solvent and even more preferably in the presence of water and DMF. It has been found that water accelerates the formation of the product. This step has been performed with up to 10-25% of water in tetrahydrofuran.

Preferred Embodiments of the Compound of Formula (I)

The compounds that may be prepared by the processes of the present invention are compounds of the formula I as previously set forth, i.e. compound of the following formula:

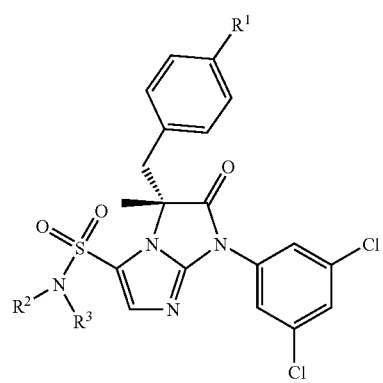

wherein:

$R^1$ is selected from bromo, trifluoromethoxy, cyano and pyrimidin-5-yl optionally mono- or di-subsituted by $NH_2$; and $R^2$ and $R^3$ are each independently selected from the group consisting of (A) hydrogen; and (B) a $C_{1-4}$ straight or branched alkyl group, optionally mono- or disubsituted with moieties independently selected from oxo, —OH, $NH_2$ and —C(O)$NR^4R^5$, where $R^4$ and $R^5$ are independently selected from:

(1) hydrogen, and
(2) a $C_{1-4}$ straight or branched alkyl group which alkyl group is mono- or disubstituted with moieties independently selected from $CONH_2$ and OH;

or $R^2$ and $R^3$, combined with the nitrogen they are bonded to, form:
  (1) a pyrrolidine or piperidine ring, each optionally substituted with the group —$C(O)NR^6R^7$, where $R^6$ and $R^7$ are independently selected from
    (A) hydrogen; and
    (B) a $C_{1-4}$ straight or branched alkyl group, optionally mono- or disubstituted with moieties independently selected from oxo, —OH and $NH_2$;
  (2) a morpholine ring; or
  (3) a piperazine ring;

or a pharmaceutically acceptable salt thereof.

In another embodiment of the compound of formula I:
$R^1$ is selected from bromo, trifluoromethoxy, cyano and pyrimidin-5-yl;
$R^2$ is H; and
$R^3$ is —$CH(R^8)C(O)NH_2$, where $R^8$ is a straight or branched $C_{1-3}$alkyl group; or
$R^2$ and $R^3$, together with the nitrogen they are bonded to form a moiety selected from

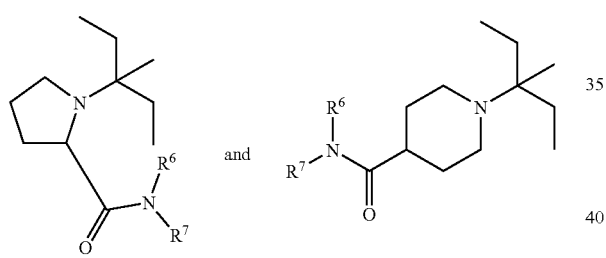

and where $R^6$ and $R^7$ are independently selected from H and straight or branched $C_{1-4}$alkyl optionally substituted with OH.

Specific examples of compounds of formula (I) that may be prepared using the process of the present invention are the following:

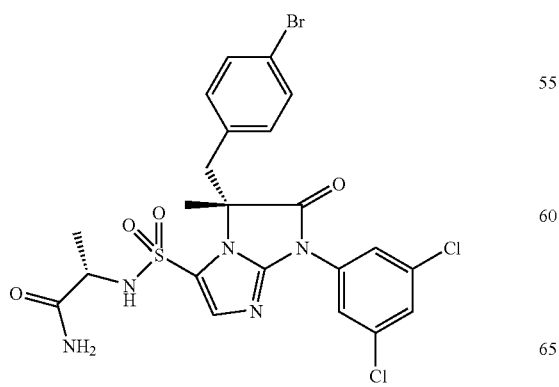

-continued

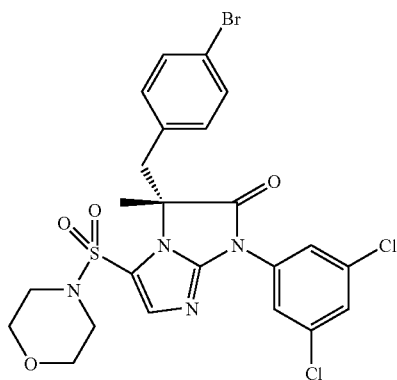

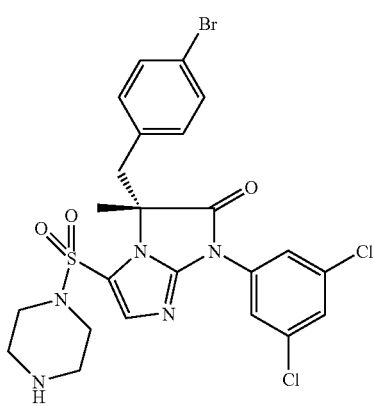

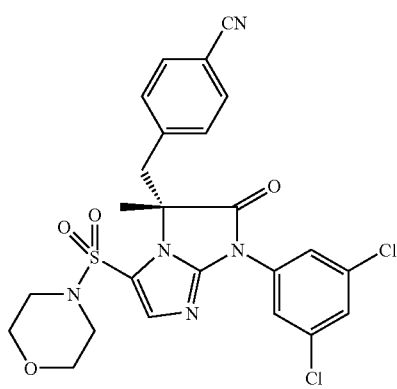

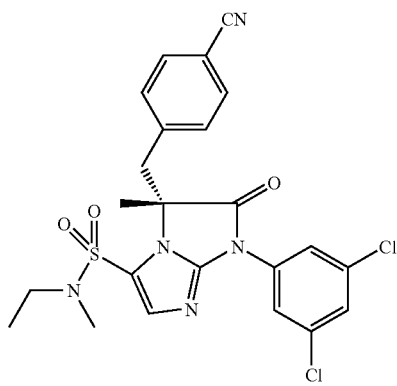

-continued

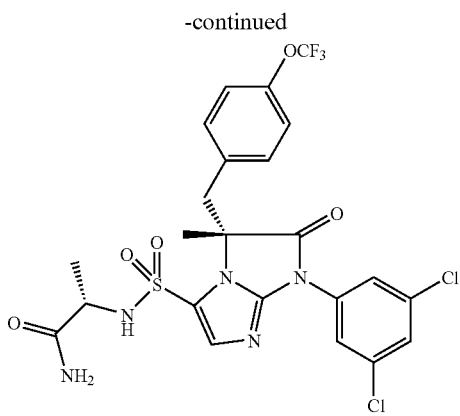

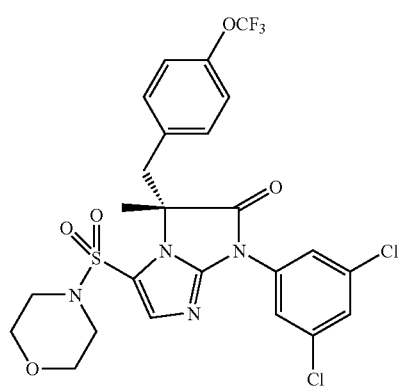

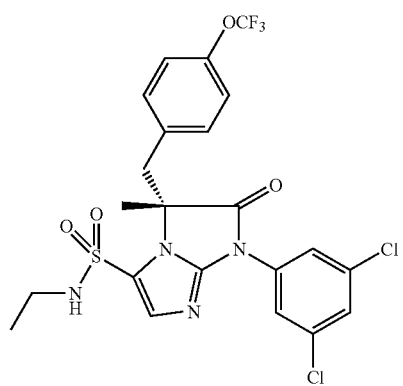

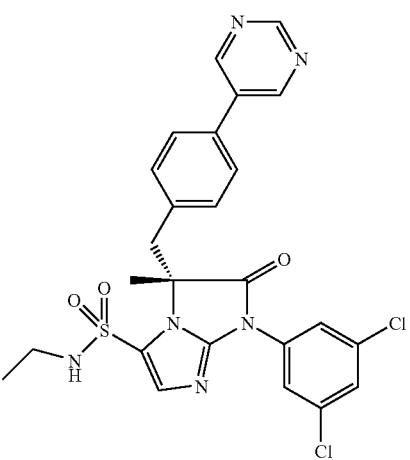

-continued

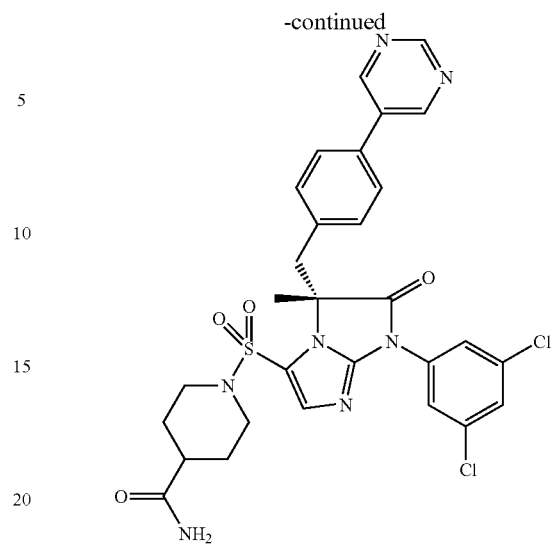

In order that this invention be more fully understood, the following examples are set forth. These examples are for the purpose of illustrating embodiments of this invention, and are not to be construed as limiting the scope of the invention in any way.

SYNTHETIC EXAMPLES

The following are representative examples that illustrate the process of the invention.

Example 1

Synthesis of (R)-3-(4-pyrimidin-5-yl-benzyl)-1-(3,5-dichlorophenyl)-5-iodo-3-methyl-1-hydroimidazo[1,2-a]imidazole-2-one

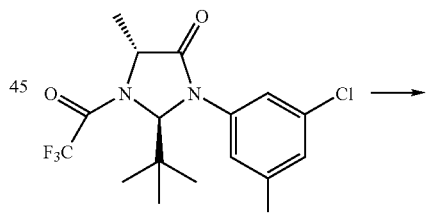

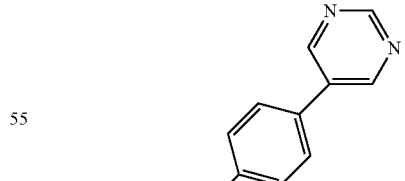

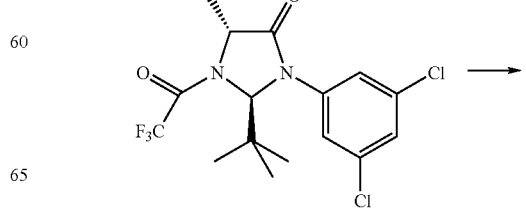

-continued

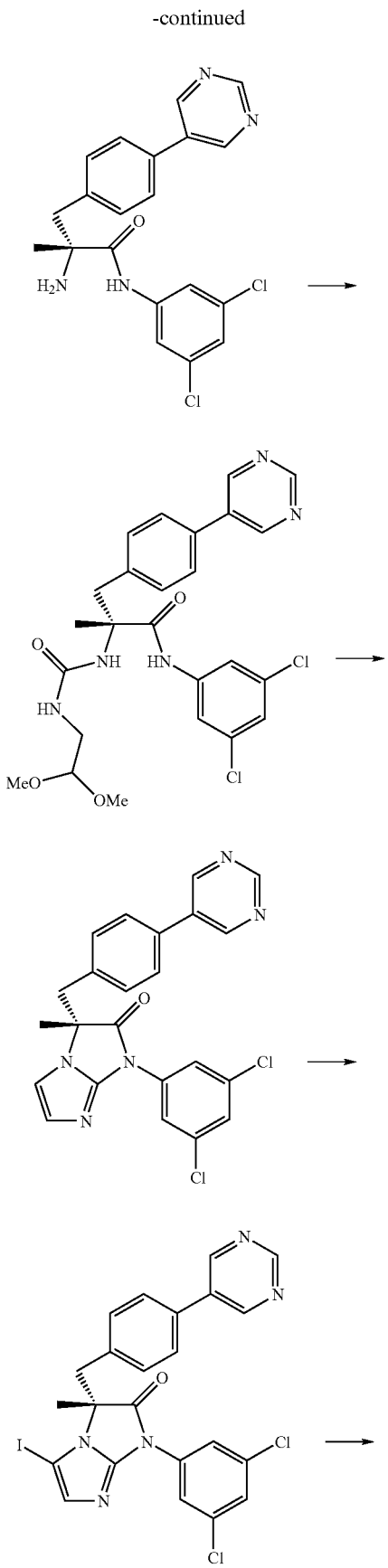

-continued

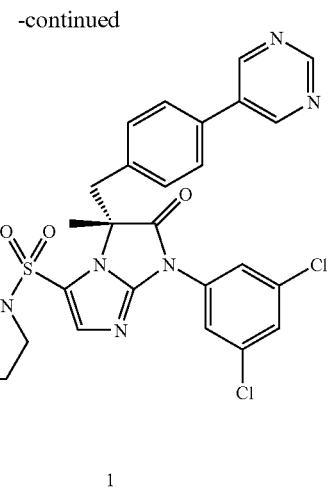

To a solution of (2S,4R)-1-(3,5-dichlorophenyl)-3-trifluoroacetyl-2-(2-tert-butyl)-4-methylimidazolidin-5-one (1.0 kg, 2.52 mol) in tetrahydrofuran (3 L) was added lithium bis(trimethylsilyl)amide (2.4 kg of 1.0 M solution in tetrahydrofuran, 2.66 mol) at 0° C. over 1 h. 4-(5-Pyrimidyl)benzyl bromide (0.63 kg, 2.52 mol) was then added in one portion. The resulting mixture was allowed to warm to 20° C. over 2 h and 10% aqueous ammonium chloride (2 L) was added. Tetrahydrofuran was evaporated under vacuum and ethyl acetate (5 L) was added. The layers were separated and the organic layer was washed with water (2 L). The organic layer was concentrated to ⅓ of its original volume and heptane (3.5 L) was added. The solid was collected by filtration to afford 1.2 kg (86%) of (2S,4R)-1-(3,5-dichlorophenyl)-3-trifluoroacetyl-2-(2-tert-butyl)-4-(4-pyrimidin-5-yl-benzyl)-4-methylimidazolidin-5-one as a light yellow solid: mp 168-169° C.: $^1$H NMR (400 MHz, CDCl$_3$) for one rotameric isomer δ 9.21 (m, 1H, ArH), 8.93 (s, 2H, ArH), 7.42 (ABq, J=8.4 Hz, 2H, ArH), 7.19 (d, J=1.6 Hz, 1H, ArH), 7.09 (ABq, J=8.4 Hz, 2H, ArH), 6.79(d, J=1.6 Hz, 2H, ArH), 5.72 (s, 1H, NCHN), 3.37 (ABq, J=14.0 Hz, 1H, ArCH$_2$), 3.24 (ABq, J=14.0 Hz, 1H, ArCH$_2$), 2.02 (s, 3H, CH$_3$), 0.75 (s, 9H, C(CH$_3$)); $^1$H NMR (400 MHz, CDCl$_3$) for the second isomer δ 9.21 (m, 1H, ArH), 8.93 (s, 2H, ArH), 7.40(ABq, J=8.4 Hz, 2H, ArH), 7.27 (t, J=1.6 Hz, 1H, ArH), 7.09 (ABq, J=8.4 Hz, 2H, ArH), 6.93 (d, J=1.6 Hz, 2H, ArH), 5.43 (s, 1H, NCHN), 3.85 (ABq, J=14.0 Hz, 1H, ArCH$_2$), 3.17 (ABq, J=14.0 Hz, 1H, ArCH$_2$), 1.99 (s, 3H, CH$_3$), 0.88 (s, 9H, C(CH$_3$)); MS: m/z 564 (M+); Anal. calcd for C$_{27}$H$_{25}$Cl$_2$F$_3$N$_4$O$_2$: C, 57.35; H, 4.46; N, 9.91. Found: C, 57.27; H, 4.44; N, 9.74.

To a solution of the above imidazolidin-5-one (150.0 g, 265.3 mmol) in tetrahydrofuran (500 mL) was added 40% trimethylbenzylammonium hydroxide (232.4 g, 557.1 mmol) followed by 50% NaOH (42.4 g, 530.5 mmol). The mixture was heated to 45° C. and stirred for 5 h. 6 N HCl (243 mL, 1.46 mol) was added dropwise to the reaction mixture keeping the internal temperature below 50° C. The mixture was stirred at 50° C. for 1 h and then the solvent was evaporated under vacuum. To this was added isopropyl acetate (750 mL) and the mixture was neutralized with 50% NaOH (63.0 g, 787.5 mmol). The layers were separated and the organic layer was washed with water (500 mL). The mixture was concentrated to one third of its original volume and heptane (600 mL) was added. The solid was collected by filtration to afford 88.4 g (83%) of (R)-2-amino-2-(4pyrimidin-5-yl-benzyl)-N-(3,5-dichlorophenyl)propionamide as a light yellow solid: mp 124-126° C.; $^1$H NMR (400 MHz, CDCl$_3$) δ 9.79 (s, 1H, ArNH), 9.18 (s, 1H, pyrimidine-H), 8.91 (s, 2H, pyrimidine-H), 7.53 (d, J=1.6 Hz, 2H, ArH), 7.52 (ABq, J=8.0 Hz, 2H, ArH), 7.35 (ABq, J=8.0 Hz, 2H, ArH), 7.06 (t, J=1.6 Hz, 1H, ArH), 3.58 (ABq, J=13.2 Hz, 1H. ArCH$_2$), 2.75 (ABq, J=13.2 Hz, 1H, ArCH$_2$), 1.51 (s, 3H, CH$_3$); $^{13}$C NMR (400 MHz, CDCl$_3$) δ 174.8, 157.5, 154.7, 139.6, 137.6, 135.2, 133.8, 133.1, 131.3, 127.1, 124.0, 117.6, 59.1, 46.0, 28.2; MS: m/z 400 (M$^+$); Anal. calcd for C$_{20}$H$_{18}$Cl$_2$N$_4$O: C, 59.86; H, 4.52; N, 13.96. Found: C, 60.14; H, 4.52; N, 13.65.

To the above propionamide (52.0 g, 129.6 mmol) in dimethyl sulfoxide (65 mL) was added a solution of phenoxycarbonylaminoacetaldehyde dimethylacetal (29.2 g, 129.6 mmol) in dimethyl sulfoxide (50 mL), followed by triethylamine (1.3 g, 13.0 mmol). The mixture was heated at 60° C. for 5 h. The reaction mixture was cooled to room temperature and to this was added 3% Na$_2$CO$_3$ (320 mL) and ethyl acetate (320 mL). The layers were separated and the organic layer was washed with water (200 mL). The organic fraction was evaporated to a low volume and heptane (400 mL) was slowly added. The resulting slurry was stirred at 22° C. for 4 h. The solid was collected by filtration to afford 62.1 g (90%) of (R)-2-[(4',4'-dimethoxyethyl)aminocarbonyl]amino-2-(4-pyrimidin-5-yl-benzyl)-N-(3,5-dichlorophenyl)-propionamide as a white solid. mp 178-179° C.: $^1$H NMR (400 MHz, CDCl$_3$) δ 9.45 (bs, 1H, NH), 9.15 (s, 1H, pyrimidine-H), 8.86 (s, 2H, pyrimidine-H), 7.44 (d, J=1.6 Hz, 2H, ArH), 7.41 (ABq, J=8.0 Hz, 2H, ArH), 7.16 (ABq, J=8.0 Hz, 2H, ArH), 6.92 (t, J=1.6 Hz, 1H, ArH), 5.97 (bs, 1H, NH), 5.90 (bs, 1H, NH), 4.23 (t, J=5.2 Hz, 1H, (CH$_3$O)$_2$CH), 3.46 (ABq, J=12.8, 1H. ArCH$_2$), 3.21 (s, 3H, CH$_3$O), 3.18 (s, 3H, CH$_3$O), 3.02 (ABq, J=12.8 Hz, ArCH$_2$), 1.24 (s, 3H, CH$_3$); $^{13}$C NMR (400 MHz, CDCl$_3$) δ 174.4, 157.8, 157.3, 154.6, 140.0, 137.4, 135.0, 134.9, 133.7, 132.5, 131.7, 126.5, 123.9, 118.6, 102.9, 60.4, 60.2, 54.2, 53.6, 23.2, 14.2; MS: m/z 531 (M$^+$); Anal. calcd for C$_{25}$H$_{27}$Cl$_2$N$_5$O$_4$: C, 56.40; H, 5.11; N, 13.15. Found: C, 55.95; H, 4.83; N, 12.86.

To a mixture of the above amide (50.0 g, 93.9 mmol), triphenylphosphine (32.0 g, 122.1 mmol) and triethylamine (13.3 g, 131.1 mmol) in acetonitrile (200 mL) was added carbon tetrachloride (20.2 g, 131.5.0 mmol) at 20° C. The mixture was stirred at 20° C. for 3 h and 4-toluenesulfonic acid monohydrate (27.1 g, 141.0 mmo) in acetonitrile (40 mL) was then added. The resulting mixture was heated at 70° C. for 2 h. Acetonitrile was evaporated under vacuum and a mixture of isopropyl acetate (250 mL) and water (250 mL) were added. The layers were separated and the organic layer was washed with 5% Na$_2$CO$_3$ (250 mL) and 3% NaCl (250 mL), respectively. The solution was concentrated to a low volume and n-propanol (200 mL) was slowly added. The mixture was heated at 70° C. for 1 h, and was then allowed to cool to 20° C. and stirred at 20° C. for 4 h. The solid was collected by filtration to afford 34.2 g of (R)-3-(4-pyrimidin-5-yl-benzyl)-1-(3,5-dichlorophenyl)-3-methyl-1-hydroimidazo[1,2-a]imidazole-2-one as a white solid: mp 170-171° C.; $^1$H NMR (400 MHz, CDCl$_3$) δ 9.17 (s, 1H, pyrimidine-H), 8.85 (s, 2H, pyrimidine-H), 7.66 (d, J=1.6 Hz, 2H, ArH), 7.39 (ABq, J=8.4 Hz, 2H, ArH), 7.21 (s, 1H, imidazole-H), 7.03 (ABq, J=8.4 Hz, 2H, ArH), 6.98 (t, J=1.6 Hz, 1H, ArH), 3.39 (ABq, J=14.0, 1H. ArCH$_2$), 3.26 (ABq, J=14.0 Hz, ArCH$_2$), 1.83 (s, 3H, CH$_3$); $^{13}$C NMR (400 MHz, CDCl$_3$) δ 174.8, 157.6, 154.7, 145.8, 135.2, 134.9, 134.1, 133.8, 133.4, 130.6, 129.2, 127.0, 120.3, 111.2, 66.2, 44.5, 23.2; MS: m/z 450 (M$^+$+1); Anal. calcd for C$_{23}$H$_{17}$Cl$_2$N$_5$O: C, 61.35; H, 3.81; N, 15.55. Found: C, 61.27; H, 3.55; N, 15.27.

To the solution of the above imidazole-2-one (14.0 g, 31.1 mmol) in methylene chloride (160 mL) was added pyridinium 4-toluenesulfonate (0.78 g, 3.1 mmol). The mixture was cooled to −5° C. and N-Iodosuccinamide (7.73 g, 34.3 mmol) was added in one portion. The mixture was stirred at 0° C. for 3 h and to this was added 2% Na$_2$SO$_3$ (60 mL). The layers were separated and the organic layer was washed with water (60 mL) and concentrated to a low volume under vacuum. Isopropanol (130 mL) was added to the residue and the mixture was heated to 50° C. for 1 h. The solution was gradually cooled to room temperature and the solid was collected by filtration to afford 24.7 g (63%) of (R)-3-(4-pyrimidin-5-yl-benzyl)-1-(3,5-dichlorophenyl)-5-iodo-3-methyl-1-ydroimidazo[1,2-a]imidazole-2-one as a light yellow solid: $^1$H NMR (400 MHz, CDCl$_3$) δ 9.17 (s, 1H, pyrimidyl-H), 8.85 (s, 2H, pyrimidyl-H), 7.49 (s, 2H, ArH), 7.38 (ABq, J=8.0 Hz, 2H, ArH), 7.27 (s, 1H, imidazole-H), 7.07 (ABq, J=8.0 Hz, 2H, ArH), 3.67 (ABq, J=14.0 Hz, 1H, CH$_2$Ar), 3.35 (ABq, J=14.0 Hz, 1H, CH$_2$Ar), 1.97 (s, 3H, CH$_3$).

A solution of the above iodoimidazole-2-one (16.5 g, 30.8 mmol) in anhydrous tetrahydrofuran (35 mL) was added to a mixture of isopropylmagnesium chloride (20.3 g of 2.0 M solution in tetrahydrofuran, 33.9 mmol) and N,N,N',N'-tetramethylethylene diamine (3.9 g, 33.9 mmol) in tetrahydrofuran (20 mL) over 20 min keeping the internal temperature below −20° C. The mixture was stirred for 10 min, at −20° C., and sulfur dioxide (2.2 g, 24.0 mmol) in anhydrous tetrahydrofuran (20 mL) was added dropwise keeping the internal temperature below −20° C. The reaction was stirred at −20° C. for 10 min and was then added to a slurry of N-chlorosuccinimide (7.2 g, 40.1 mmol) in anhydrous tetrahydrofuran (30 mL). The mixture was stirred for 10 min at 0° C. To the resulting mixture were added isonipecotamide (4.0 g, 56.0 mmol), diisopropylethylamine (6.4 mL, 37.0) and water (35 mL). The mixture was allowed to warm to 22° C. and stirred at 22° C. for 2 h. Water (70 mL) and ethyl acetate (40 mL) were then added to the reaction mixture and the layers were separated. The organic layer was washed with 0.5 N HCl (70 mL) and water (70 mL). The organic fraction was evaporated to a low volume andisopropanol (120 mL) was added. The solution was then concentrated. The residual product was crystallized from isopropanol. The solid was collected by filtration to afford 14.1 g (75%) of the title compound as a white solid. $^1$H NMR (400 MHz, CDCl$_3$) δ 9.17 (s, 1, ArH), 8.84 (s, 2H, ArH), 7.38-7.09 (m, 8H, ArH), 5.59 (bs, 1H, NH), 5.53 (bs, 1H, NH), 3.95 (ABq, J=13.9 Hz, CH$_2$Ar), 3.93 (m, 1H, NCH$_2$), 3.80 (m, 1H, NCH$_2$), 3.31 (ABq, J=13.9 Hz, 1H, CH$_2$Ar), 2.90 (m, 2H, NCH$_2$), 2.33 (m, 1H, CHCONH$_2$), 2.05 (m, 1H, CH$_2$), 2.02 (s, 3H, CH$_3$), 1.83-1.97 (m, 3H, CH$_2$). $^{13}$C NMR (400 MHz, CDCl$_3$) δ 175.7, 173.9, 157.5, 154.7, 149.0, 135.8, 135.4, 134.1, 133.8, 133.4, 133.3, 130.3, 128.0, 127.0, 123.9, 121.3, 70.5, 45.1, 44.8, 43.1, 41.0, 28.1, 28.0, 22.5. MS: m/z 605 (M$^+$); Anal. calcd for C$_{29}$H$_{27}$Cl$_2$N$_7$O$_4$S: C, 54.38; H, 4.25; Cl, 11.07; N, 15.31; S, 5.01. Found: C, 54.31; H, 4.15; Cl, 10.74; N, 15.17; S, 5.15.

Example 2

Synthesis of 2(S)-[7-(3,5-Dichlorophenyl)]-5(R)-methyl-6-oxo-5-(4-bromobenzyl)-6,7-dihydro-5H-imidazo[1,2-a]imidazole-3-sulfonylamino]propionamide

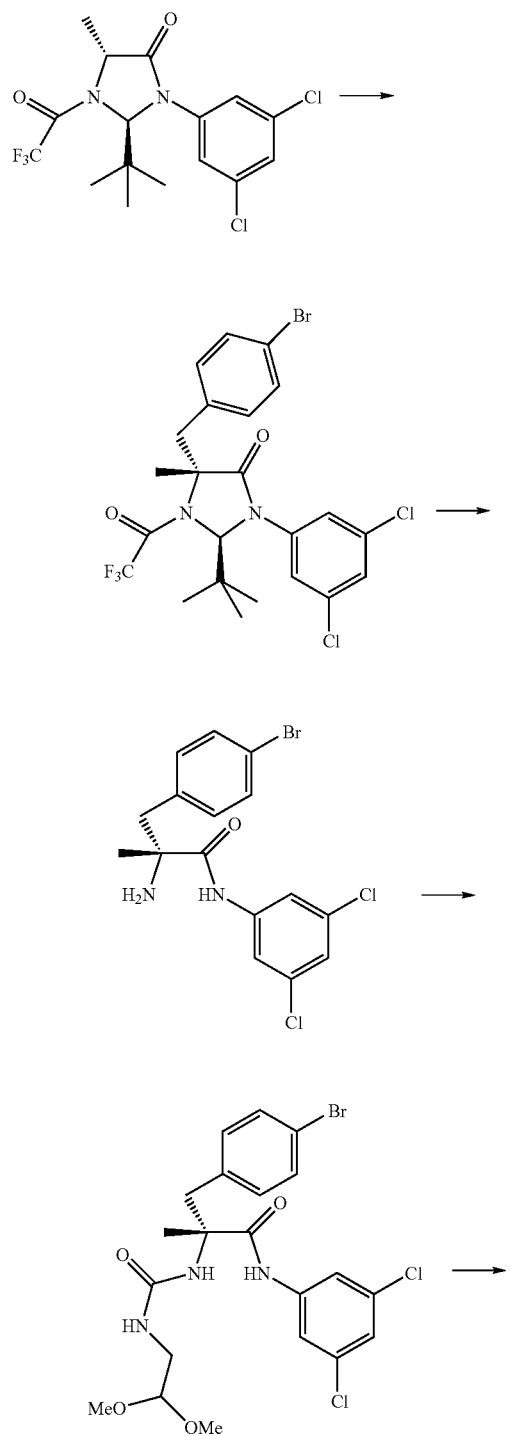

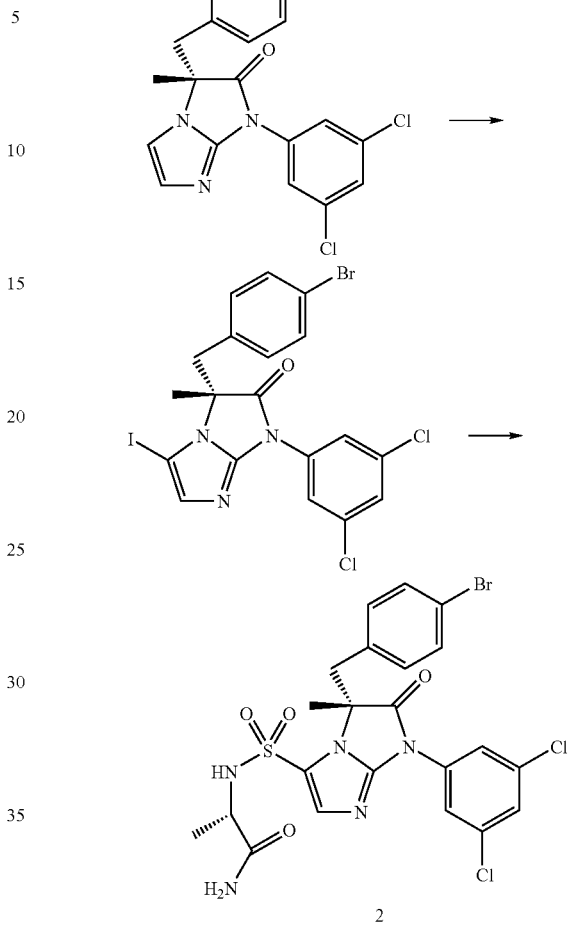

To a solution of (2S,4R)-1-(3,5-dichlorophenyl)-3-trifluoroacetyl-2-(2-tert-butyl)-4-methylimidazolidin-5-one (1.62 kg, 4.08 mol) in tetrahydrofuran (24 L) was added lithium bis(trimethylsilyl)amide (3.86 kg of 1.0 M solution in tetrahydrofuran, 4.34 mol) at 0° C. over 1 h. 4-bromobenzyl bromide (1.05 kg, 4.21 mol) in tetrahydrofuran (1.7 L) was then added over 1 h keeping the internal temperature below 0° C. The resulting mixture was stirred for 30 min and 10% aqueous ammonium chloride (3.6 L) was added. Tetrahydrofuran was evaporated under vacuum and the slurry was filtered. The filter cake was washed with water (6 L) and the filterate was stirred with 10:1 mixture of heptane and ethyl acetate (2.5 L) for 30 min. The solid was collected by filtration to afford 2.10 Kg (91%) of (2S,4R)-1-(3,5-dichlorophenyl)-3-trifluoroacetyl-2-(2-tert-butyl)-4-(4-bromobenzyl)-4-methylimidazolidin-5-one as a white solid: $^1$H NMR (400 MHz, CDCl$_3$) for one rotameric isomer δ 7.21 (d, J=1.8 Hz, 2H, ArH), 7.19 (ABq, J=8.4 Hz, 2H, ArH), 6.87 (d, J=1.8 Hz, 1H, ArH), 6.72 (ABq, J=8.4 Hz, 2H, ArH), 5.60 (s, 1H, NCHN), 3.65 (ABq, J=14.0 Hz, 1H, ArCH$_2$), 3.04 (ABq, J=14.0 Hz, 1H, ArCH$_2$), 1.90 (s, 3H, CH$_3$), 0.67 (s, 9H, C(CH$_3$)); $^1$H NMR (400 MHz, CDCl$_3$) for the second isomer δ 7.21 (d, J=1.8 Hz, 2H, ArH), 7.18 (ABq, J=8.4 Hz, 2H, ArH), 6.87 (d, J=1.8 Hz, 1H, ArH), 6.70 (ABq, J=8.4 Hz, 2H, ArH), 5.40 (s, 1H, NCHN), 3.20 (ABq, J=14.0 Hz, 1H, ArCH$_2$), 3.00 (ABq, J=14.0 Hz, 1H, ArCH$_2$), 1.87 (s, 3H, CH$_3$), 0.80 (s, 9H, C(CH$_3$)); MS: m/z 566 (M$^+$).

To a solution of the above imidazolidin-5-one (2.0 Kg, 3.50 mol) in tetrahydrofuran (7.0 L) was added 40% trimethylbenzylammonium hydroxide (3.07 Kg, 7.35 mol) followed by 50% NaOH (0.56 Kg, 7.00 mol). The mixture was heated to 45° C. and stirred for 5 h. 6 N HCl (3.2 L, 19.20 mol) was added dropwise keeping the internal temperature below 50° C. The mixture was stirred at 50° C. for 1 h and the THF was then evaporated under vacuum. Isopropyl acetate (10 L) was added and the mixture was neutralized with 50% NaOH (0.84 Kg, 10.5 mol). The layers were separated and the organic layer was washed with water (6.7 L). Isopropyl acetate was evaporated under vacuum and dimethyl sulfoxide (3.5 L) was added. A quantitative assay by HPLC showed 1.41 Kg (99%) of (R)-2-amino-2-(4-bromobenzyl)-N-(3,5-dichlorophenyl) propionamide in dimethyl sulfoxide. The dimethyl sulfoxide solution containing the crude reaction product was used directly in the next step without purification. A small sample of the product as its 4-toluenesulfonic acid salt was isolated as a white solid by crystallization from acetonitrile for characterization: mp>200° C.; $^1$H NMR (400 MHz, $(D_3C)_2SO$) δ 10.44 (s, 1H, ArNH), 8.30 (bs, 2H, $NH_2$), 7.71 (d, J=1.6 Hz, 2H, ArH), 7.51 (ABq, J=6.4 Hz, 2H, ArH), 7.37 (t, J=1.6 Hz, 1H, ArH), 7.28 (ABq, J=7.4 Hz, 2H, ArH), 7.11 (ABq, J=6.4 Hz, 2H, ArH), 6.81 (ABq, J=7.4 Hz, 2H, ArH), 3.40 (ABq, J=14.0, 1H. $ArCH_2$), 3.20 (ABq, J=14.0 Hz, $ArCH_2$), 2.27 (s, 3H, $CH_3$), 2.27 (s, 3H, $CH_3$), 1.66 (s, 3H, $CH_3$); MS: m/z 402 ($M^+$).

To a solution of phenoxycarbonylaminoacetaldehyde dimethylacetal (0.91 Kg, 4.03 mol) in dimethyl sulfoxide (3.3 L) was added the above propionamide, followed by triethylamine (33 g, 34 mol). The mixture was heated at 60° C. for 5 h and 3% $Na_2CO_3$ (10 L) was added. The layers were separated and the organic layer was washed with water (6.7 L). Ethyl acetate was evaporated to a low volume and heptane (12 L) was slowly added. The resulting slurry was stirred at 22° C. for 4 h. The solid was collected by filtration to afford 1.67 Kg (89%) of (R)-2-[(4',4'-dimethoxyethyl)aminocarbonyl] amino-2-(4-bromobenzyl)-N-(3,5-dichlorophenyl)-propionamide as a white solid. mp: 128-130° C. $^1$H NMR (400 MHz, $CDCl_3$) δ 9.94 (bs, 1H, NH), 7.79 (d, J=1.8 Hz, 2H, ArH), 7.46 (ABq, J=8.3 Hz, 2H, ArH), 7.22 (t, J=1.8 Hz, 1H, ArH), 7.07 (ABq, J=8.3 Hz, 2H, ArH), 6.17 (bs, 1H, NH), 6.12 (t, J=4.4 Hz, 1H, NH), 4.35 (t, J=5.3 Hz, 1H, $(CH_3O)_2CH$), 3.38 (ABq, J=12.4, 1H. $ArCH_2$), 3.30 (s, 6H, $CH_3O$), 3.30-3.25 (m, 2H, $CH_2NH$), 3.08 (ABq, J=12.4 Hz, $ArCH_2$), 1.15 (s, 3H, $CH_3$). MS: m/z 502 ($M^+$-$OCH_3$).

To a mixture of the above amide (1.60 Kg, 3.00 mol), triphenylphosphine (1.01 Kg, 3.86 mol) and triethylamine (419 g, 4.14 mol) in acetonitrile (6 L) was added carbon tetrachloride (640 g, 4.16 mol) at 20° C. The mixture was stirred at 20° C. for 3 h and 4-toluenesulfonic acid monohydrate (848 g, 4.45 mol) in acetonitrile (12 L) was then added. The resulting mixture was heated to 70° C. for 2 h. Acetonitrile was evaporated under vacuum, isopropyl acetate (8 L) and water (8 L) were added. The layers were separated and the organic layer was washed with 5% $Na_2CO_3$ (8 L) and 3% NaCl (8 L), respectively. The solution was concentrated to a low volume and heptane (8 L) was slowly added. The slurry was filtered and the filtrate was concentrated to a low volume. The residue was dissolved in dimethoxyethane (2.5 L). A quantitative assay by HPLC showed 1.27 g (94%) of (R)-3-(4-bromobenzyl)-1-(3,5-dichlorophenyl)-3-methyl-1-hydroimidazo[1,2-a]imidazol-2-one in dimethoxyethane. The solution of the crude product was used directly in the next step without purification.

To the solution of the imidazol-2-one from the above step (30.9 g, 67.7 mmol) in dimethoxyethane (350 mL) was added pyridinium p-toluenesulfonate (1.71 g, 6.8 mmol). The mixture was cooled to −5° C. and N-Iodosuccinimide (16.83 g, 74.8 mmol) was added in one portion. The mixture was stirred at 0° C. for 3 h and ethyl acetate (124 mL) and 2% $Na_2SO_3$ (124 mL) were added to the reaction mixture. The layers were separated. The organic layer was washed with water (100 mL) and concentrated to a low volume under vacuum. Isopropanol (130 mL) was added to the residue and the mixture was heated to 50° C. for 1 h. The solution was then gradually cooled to room temperature. The solid was collected by filtration to afford 24.7 g (63%) of (R)-3-(4-bromobenzyl)-1-(3,5dichlorophenyl)-5-iodo-3-methyl-1-hydroimidazo[1,2-a]imidazol-2-one as a light yellow solid: mp 120-122° C.; $^1$H NMR (400 MHz, $CDCl_3$) δ 7.56 (d, J=1.8 Hz, 2H, ArH), 7.28 (ABq, J=8.4 Hz, 2H, ArH), 6.96 (s, 1H, ArH), 6.80 (ABq, J=8.4 Hz, 2H, ArH), 3.55 (ABq, J=14.0 Hz, 1H, $CH_2Ar$), 3.26 (d, J=14.0 Hz, 1H,$CH_2Ar$), 1.93 (s, 3H, $CH_3$). MS: m/z 577 ($M^+$).

A solution of the above iodoimidazol-2-one (50.0 g, 93.4 mmol) in anhydrous THF (150 mL) was cooled to −25° C. A solution of iPrMgCl in THF (49.0 mL, 98.1 mmol, 2.0M/THF) was added through an addition funnel over 20-30 min, keeping the temperature between −20 and −25° C. The reaction mixture was stirred at −20° C. for 20 min after the addition was complete. A solution of $SO_2$ in THF (33.7 g, 107.4 mmol, ~33 mL, 20.4 w/w % $SO_2$ in THF) was added to the reaction mixture at −20 to −25° C. over 15-20 min. The reaction mixture was slowly warmed up to about 20° C. over 1.5 h to ensure the completion of the reaction. To a separate 1000 mL three neck flask was added solid N-chlorosuccimimide (17.5 g, 130.8 mmol) and THF (75 mL). The stirred slurry was then cooled to −5° C. The intermediate $SO_2$ adduct in THF was transferred through a cannula to the N-chlorosuccinimide-THF slurry over 20-30 min, keeping the temperature below 0° C. The resulting mixture was stirred at about 0° C. for 0.5 h. At about 0° C., solid cesium carbonate (45.6 g, 140.1 mmol) and L-alaninamide hydrochloride (23.3 g, 186.8 mmol) were added, followed by water (51 mL) and DMF (61.4 mL). (Note: Water/THF vol/vol is 1:6, DMF/THF vol/vol is 1:5.)

The reaction mixture was allowed to warm up to 20 to 22° C. over 0.5 h was and stirred at that temperature for another 6 to 7 h. EtOAc (120 mL) and water (200 mL) were added to the reaction mixture. The mixture was stirred for 10 min and was allowed to settle for phase separation. The layers were separated and the aqueous layer was removed. The organic layer was distilled under vacuum (~165 torr) to the minimum agitation level, keeping bath temperature lower than 45° C. EtOAc (250 mL) and 10% $K_2CO_3$ solution (200 mL) were added to the residue and the mixture was stirred for 10 min. The organic layer was separated and stirred with 0.5 N HCl (200 mL) for 10 min. The organic layer was then separated and stirred with 2% NaCl (200 mL) for 10 min. The organic layer was then distilled under vacuum (~88 torr) to the minimum agitation level, keeping the bath temperature lower than 45° C. To the residue of distillation was added EtOAc (100 mL). The mixture was heated to 65° C. and became a clear solution. At that temperature, heptane (600 mL) was added over 1 h. After the addition, the slurry was stirred for 0.5 h at 65° C. and then was cooled to 20 to 22° C. over 2 h. The stirring was continued at that temperature for 2 more h. The solid was filtered, washed with 1:6 EtOAc/heptane (170 mL) and dried under vacuum at 40° C. to provide 47.5 g of the title compound as an ethyl acetate solvate: white solid, mp 110-112° C.; $^1$H NMR (400 MHz, $CDCl_3$) δ 7.43 (s, 1H, ArH), 7.38 (s, 2H, ArH), 7.32 (s, H, ArH), 7.27 (ABq, J=8.4 Hz, 2H, ArH), 6.83 (ABq, J=8.0 Hz, 2H, ArH), 6.78 (d, J=6.5 Hz, 1H, NH), 6.49 (s, 1H, $NH_2$), 6.41 (s, 1H, $NH_2$), 4.04 (m, 1H, $CHCONH_2$), 3.81 (ABq, J=12.0 Hz, 1H, $CH_2Ar$), 3.22 (ABq, J=12.0 Hz, $CH_2Ar$), 2.00 (s, 3H, $CH_3$), 1.38 (d, J=8.0 Hz, 3H, $CH_3$). $^{13}$C NMR (400 MHz, $CDCl_3$) δ 173.2, 172.7, 148.2, 134.7, 134.5, 132.4, 131.0, 130.7, 129.8, 127.0, 124.8, 121.2, 120.1, 69.1, 51.2, 41.6, 21.1, 18.2. MS: m/z 601 ($M^+$).

The compounds listed below may be prepared by a similar procedure, using an appropriate iodoimidazolone or bromoimidazolone intermediate of formula XXII wherein Y is either iodo or bromo:

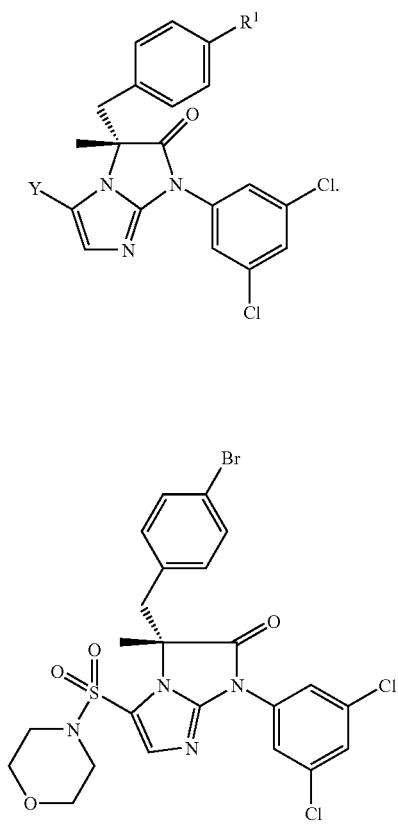

<sup>1</sup>H NMR (500 MHz, CDCl<sub>3</sub>) δ 7.41 (d, J=1.8 Hz, 2H, ArH), 7.34 (s, 1H, imidazole-H), 7.28 (t, J=1.8 Hz, 1H, ArH), 7.23 (ABq, J=8.4 Hz, 2H, ArH), 6.79 (ABq, J=8.4 Hz, 2H, ArH), 3.78 (m, 5H), 3.21 (m, 5H), 1.95 (s, 3H, CH<sub>3</sub>), <sup>13</sup>C NMR (500 MHz, CDCl<sub>3</sub>) δ 172.0, 147.2, 134.1, 133.5, 131.7, 130.1, 129.8, 128.9, 126.0, 121.1, 120.3, 119.2, 69.7, 45.9, 44.8, 42.3, 22.2. MS: m/z 600 (M<sup>+</sup>).

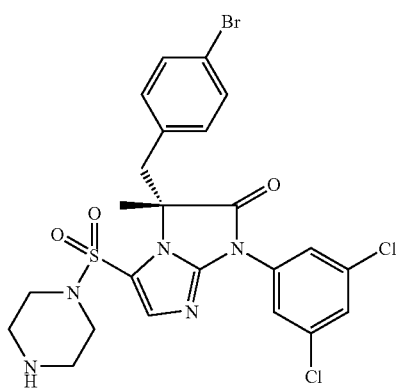

$^1$H NMR (500 MHz, CDCl$_3$) δ 7.41 (d, J=1.8 Hz, 2H, ArH), 7.34 (s, 1H, imidazole-H), 7.31 (t, J=1.8 Hz, 1H, ArH), 7.25 (ABq, J=8.4 Hz, 2H, ArH), 6.82 (ABq, J=8.4 Hz, 2H, ArH), 3.82 ((ABq, J=13.4 Hz, 1H, ArCH$_2$), 3.24 (m, 5H), 3.00 (m, 4H), 1.97 (s, 3H, CH$_3$), $^{13}$C NMR (500 MHz, CDCl$_3$) δ 171.9, 147.2, 134.1, 133.5, 131.7, 130.1, 129.8, 128.9, 126.0, 121.1, 120.3, 119.2, 68.4, 64.1, 43.8, 40.9, 20.8. MS: m/z 600 (M$^+$).

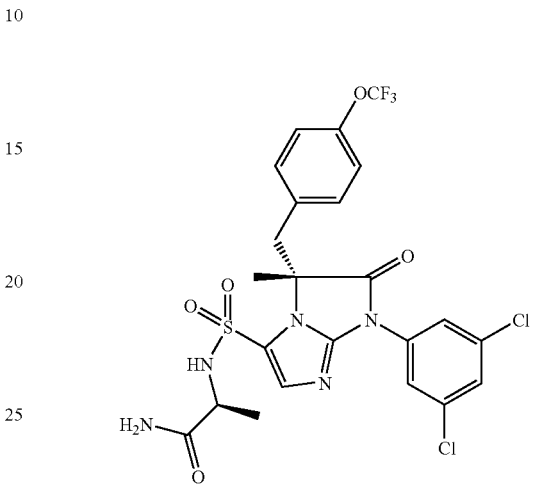

mp 96-99° C.; $^1$H NMR (400 MHz, DMSO-d$_6$) δ 8.40 (Bs, 1H, NH), 7.64 (s, 1H, ArH), 7.46 (s, 2H, ArH), 7.44 (bs, 2H, NH2), 7.16 (ABq, J=8.0 Hz, 2H, ArH), 7.00 (ABq, J=8.0 Hz, 2H, ArH), 3.75 (m, 1H, CHCONH$_2$), 3.77 (ABq, J=12.0 Hz, 1H, CH$_2$Ar), 3.29 (ABq, J=12.0 Hz, CH$_2$Ar), 1.97 (s, 3H, CH$_3$), 1.22 (d, J=8.0 Hz, 3H, CH$_3$). MS: m/z 605 (M$^+$); Anal. calcd for C$_{23}$H$_{20}$Cl$_2$F$_3$N$_5$O$_5$S: C, 45.55; H, 3.32; Cl, 11.69; F, 9.40; S, 5.29. N, 11.55. Found: C, 45.56; H, 3.01; Cl, 11.54; F, 9.79; S, 5.29. N, 11.41.

$^1$H NMR (400 MHz, CDCl$_3$) δ 7.39 (d, J=1.8 Hz, 2H, ArH), 7.36 (s, 1H, imidazole-H), 7.27 (t, J=1.8 Hz, 1H, ArH), 7.00 (ABq, J=8.4 Hz, 2H, ArH), 6.96 (Abq, J=8.4 Hz, 2H, ArH), 3.88 (ABq, J=13.4 Hz, 1H, ArCH$_2$), 3.26 (ABq, J=13.4 Hz, 1H, ArCH$_2$), 3.15 (m, 2H, NHCH$_2$), 1.99 (s, 3H, CH$_3$), 1.20 (t, J=6.8 Hz, 3H, CH$_3$). MS: m/z 558 (M$^+$).

Examples 3 and 4 illustrate alternative processes for the steps in Examples 1 and 2 for the cyclization of the urea intermediate to the imidazol-2-one.

Example 3

Synthesis of (R)-3-(4-bromobenzyl)-1-(3,5-dichlorophenyl)-3-methyl-1-hydroimidazo[1,2-a]imidazol-2-one

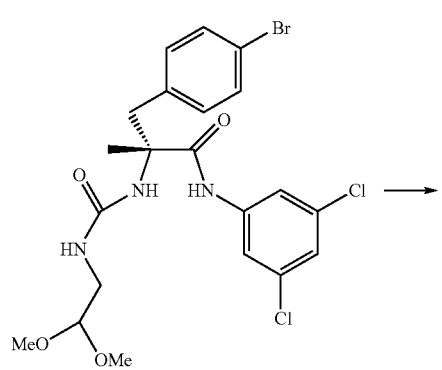

Example 4

Synthesis of (R)-3-(4-pyrimidin-5-yl-benzyl)-1-(3,5-dichlorophenyl)-3-methyl-1-hydroimidazo[1,2-a]imidazole-2-one

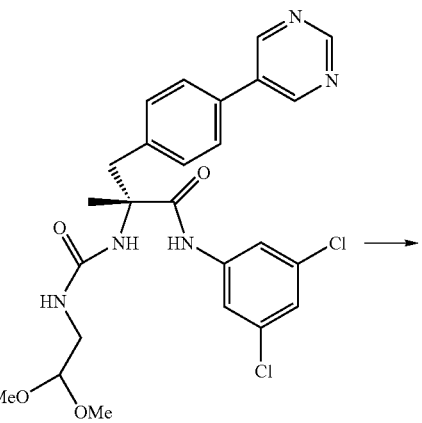

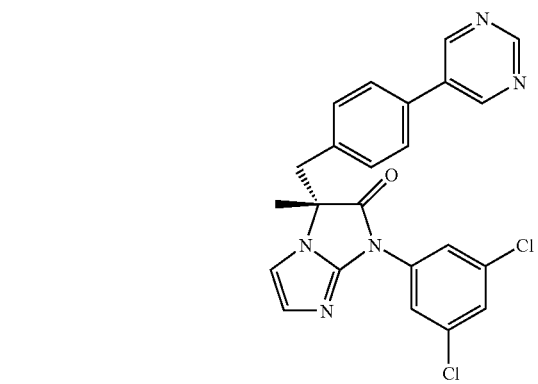

To a mixture of the (R)-2-[(4',4'-dimethoxyethyl)aminocarbonyl]amino-2-(4-bromobenzyl)-N-(3,5-dichlorophenyl)-propionamide (20 g, 37.15 mmol) and Et₃N (14.3 g, 141.2 mmol) in MeCN (50 mL) was added dichlorotriphenylphosphorane (21.6 g, 66.86 mmol) in MeCN (50 mL) over 30 min at 0° C., keeping the internal temperature below 10° C. The mixture was stirred at 25° C. for 30 min and p-toluenesulfonic acid monohydrate (27.5 g, 144.6 mmol) was added. The solution was heated to 70° C. for 30 min. MeCN was removed and isopropyl acetate (200 mL) was added. The organic solution was washed with H₂O (150 mL), 5% Na₂CO₃ (150 mL) and 3% NaCl (150 mL), respectively. Solvent was removed and the residue oil was slurried in 10:1 heptane/isopropyl acetate (242 mL) for 16 h. The mixture was filtered and the cake was washed with 10:1 heptane/isopropyl acetate (44 mL). The filtrate was concentrated to a low volume. The residue was dissolved in dimethoxyethane (200 mL). A quantitative assay by HPLC showed 16.1 g (95%) of product in dimethoxyethane. The solution of the crude product was used directly in the halogenation step.

(R)-2-[(4',4'-Dimethoxyethyl)aminocarbonyl]amino-2-(4-pyrimidin-5-yl-benzyl)-N-(3,5-dichlorophenyl)-propionamide (1.5 g, 2.82 mmol) was slurried with MeCN (7 mL) and Et₃N (1.08 g, 10.72 mmol) at 0° C. Dichlorotriphenylphosphorane (1.64 g, 5.08 mmol) in MeCN (8 mL) was added over 30 min, keeping internal temperature below 10° C. The mixture was stirred at 25° C. for 30 min. MeCN was removed and EtOAc (15 mL) was added. The organic solution was extracted two times with 1N HCl (10 mL each) and discarded. The aqueous solution was washed two times with EtOAc (5 mL). The aqueous solution was then mixed with EtOAc (20 mL) and the pH was adjusted to 8 by addition of 10% NaOH. The organic layer was collected and p-toluenesulfonic acid monohydrate (2.09 g, 11.0 mmol) was added. The solution was heated to 67° C. for 1 h. The pH was adjusted to 7 by addition of 10% NaOH. The organic solution was washed with 3% NaCl (10 mL). Solvent was removed and the residue oil was slurried in 2:1 heptane/EtOAc (5 mL) for 16 h. The solid was collected by filtration to afford 1.02 g (80%) of the title compound.

Example 5

Cyclization of Urea Intermediates Using Boronic Acids

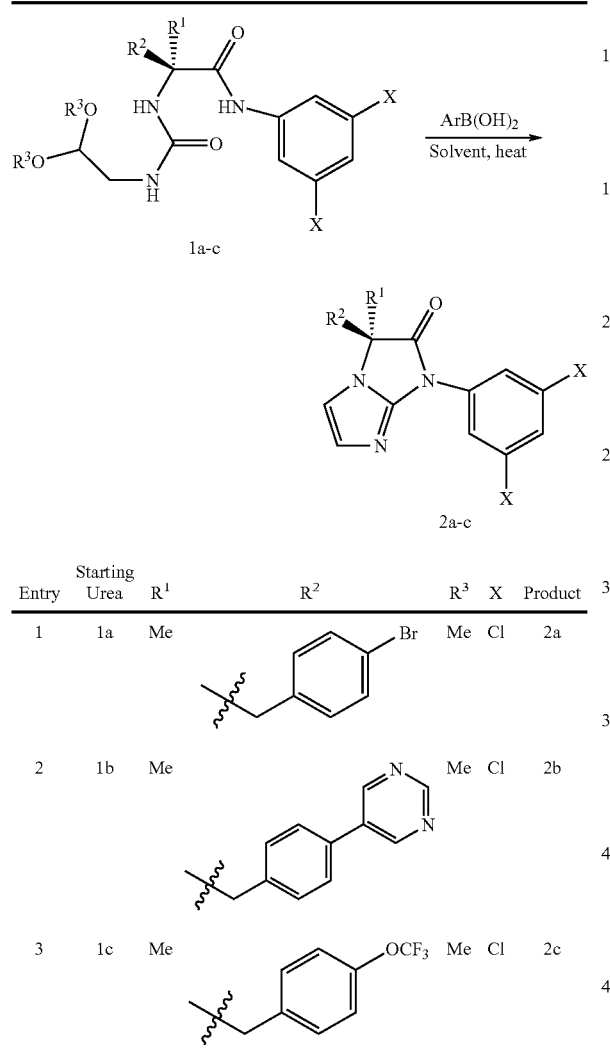

| Entry | Starting Urea | R¹ | R² | R³ | X | Product |
|---|---|---|---|---|---|---|
| 1 | 1a | Me | (4-bromobenzyl) | Me | Cl | 2a |
| 2 | 1b | Me | (4-pyrimidin-5-yl-benzyl) | Me | Cl | 2b |
| 3 | 1c | Me | (4-trifluoromethoxybenzyl) | Me | Cl | 2c |

A solution of 1a (0.50 g, 0.93 mMol) in toluene (10 mL) was charged in a reaction vessel equipped with a Dean Stark distillation trap, magnetic stirring and nitrogen line was treated at room temperature with a catalytic amount of 3,5-bis(trifluoromethyl)phenyleboronic acid (0.036 g, 0.14 mMol, 0.15 eq.). The reaction mixture was heated to reflux for 5 hours. The solvent was removed under reduced pressure and the residue was purified on a CombiFlash instrument using EtOAc-hexane, (from 100% hexanes to 70% hexanes). Removal of solvent under reduced pressure gave 0.23 g of pure product 2a as a white solid in 54% yield: ¹H NMR (300 MHz,CDCl₃) δ 9.18 (s, 1H), 8.86 (s, 2H), 7.65 (d, J=1.5 Hz, 2H), 7.41 (d, J=6.0 Hz, 2H), 7.24 (dd, J=1.5, 1.2 Hz, 1H), 7.04 (d, J=6.0 Hz, 2H), 6.99 (dd, J=8.7, 1.2 Hz, 2H), 3.26 (d, J=40.8, 10.2 Hz, 2H), 1.76 (s, 3H); ¹³C NMR (300 MHz, CDCl₃) δ 174.8, 157.6, 154.8 (2C), 145.8, 135.3 (2C), 134.9, 134.2, 133.8, 133.4, 130.6 (2C), 129.1, 127.2 (2C), 127.0 (2C), 120.4, 111.2, 66.3, 44.5, 23.3.

Products 2b and 2c were prepared by a procedure similar to that employed to prepare product 2a but using the appropriate starting urea compound 1b or 1c.

2b: ¹H NMR (300 MHz,CDCl₃) δ 7.72 (d, J=1.2 Hz, 2H), 7.29 (d, J=6.3 Hz, 2H), 7.25 (s, 1H), 6.95 (s, 1H), 6.90 (s, 1H), 6.76 (d, J=6.3 Hz, 2H), 3.20 (d, J=40.8, 10.2 Hz, 2H), 1.76 (s, 3H); ¹³C NMR (300 MHz, CDCl₃) δ 174.8, 145.7, 135.3, 134.8 (2C), 132.0 (2C), 131.7, 131.2 (2C), 128.8, 127.1, 122.13, 120.3, 120.0, 111.3, 66.1, 44.0, 23.2.

2c: ¹H NMR (400 MHz,CDCl₃) δ 7.69 (m, 2H), 7.26 (m, 1H), 7.03 (s, 1H), 7.01 (s, 1H), 6.97 (m, 1H), 6.92 (s, 1H), 6.90 (m, 2H), 3.3-3.20 (dd, J=50.6, 13.9 Hz, 2H), 1.78(s, 3H); ¹³CNMR (400 MHz, CDCl₃) δ 174.8, 148.9, 145.8, 135.4, 134.8, 131.8, 130.9, 129.2, 127.1, 120.9, 120.2, 111.1, 66.1, 44.0, 23.2.

Examples 6 and 7 illustrate the preparation of alternative intermediates that may be employed in the processes of the present invention.

Example 6

Synthesis of (R)-3-(4-bromobenzyl)-1-(3,5-dichlorophenyl)-5-bromo-3-methyl-1-hydroimidazo[1,2-a]imidazole-2-one

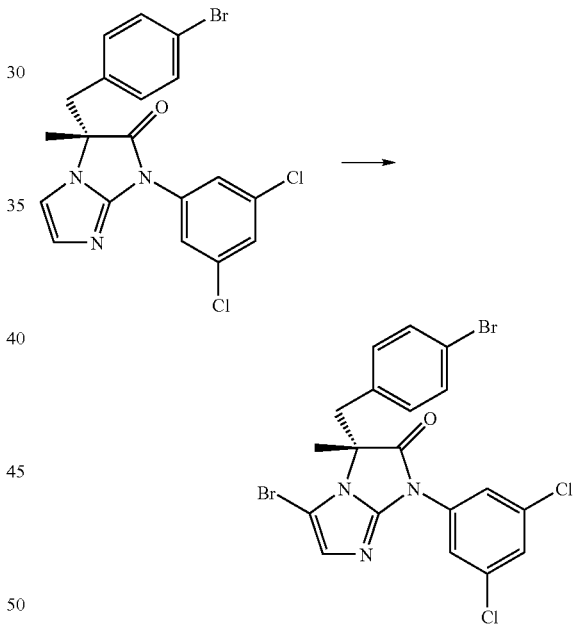

To a solution of of (R)-3-(4-bromobenzyl)-1-(3,5-dichlorophenyl)-3-methyl-1-hydroimidazo[1,2-a]imidazol-2-one (7.0 g, 15.3 mmol) in dimethoxyethane (15 mL) was added triethylamine (0.15 g, 1.5 mmol), and the mixture was cooled to −5° C. N-Bromosuccinimide (3.95 g, 22.2 mmol) in dimethoxyethane (40 mL) was added over 2 h keeping the internal temperature below 0° C. 0.5% Na₂SO₃ (4 mL) was then added, and the mixture was concentrated under vacuum. Ethyl acetate (35 mL) and water (20 mL) were added to the reaction mixture and the layers were separated. The organic layer was washed with water (20 mL) and concentrated. The residue was purified by chromatography to afford 6.26 g (77%) of the title compound. ¹H NMR (400 MHz, CDCl₃) δ 7.60 (d, J=1.8 Hz, 2H, ArH), 7.26 (ABq, J=8.4 Hz, 2H, ArH), 7.25 (s, 1H, ArH), 6.83 (s, 1H, imidazole-H), 6.80 (ABq, J=8.4 Hz, 2H, ArH), 3.46 (ABq, J=14.0, 1H. ArCH$_2$), 3.27 (ABq, J=14.0 Hz, ArCH2), 1.90 (s, 3H, CH$_3$). MS m/z 530 (M$^+$).

Example 7

Synthesis of (R)-2-amino-2-(4-trifluoromethoxybenzyl)-N-(3,5-dichlorophenyl)propionamide

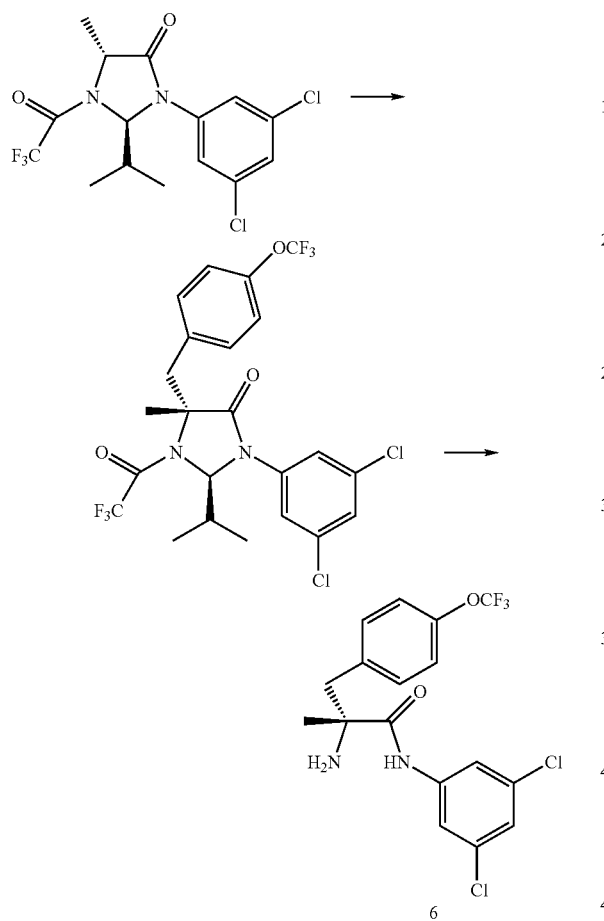

To a solution of (2S,5R)-3-(3,5-dichloro-phenyl)-2-isopropyl-5-methyl-1-(2,2,2-trifluoro-acetyl)-imidazolidin-4-one (50.0 g, 130.0 mmol) and 4-trifluoromethoxybenzyl bromide (33.94 g, 133.0 mmol) in THF (200 mL) was added lithium bis(trimethylsilyl)amide (136.5 mL of 1.0 M solution in THF, 136.5 mmol) at 0° C. over 20 min keeping the internal temperature below 0° C. The resulting mixture was stirred at for 30 min. 10% Aqueous ammonium chloride (160 mL) and EtOAc (100 mL) were added. The layers were separated and the organic layer was concentrated to dryness. To the residue was added 2-propanol (250 mL) and potassium hydroxide (9.89 g, 176 mmol), and the mixture was heated at 50° C. for 4 h. 3 M H$_2$SO$_4$ (32 mL) was then added and the mixture was heated at 70° C. for 2 h. 2-Propanol was distilled and isopropyl acetate (200 mL) was added. The organic solution was washed with 2 N NaOH (200 mL) and water (150 mL) and then concentrated to dryness. Acetonitrile (150 mL) was added to the residue followed by 4-toluenesulfonic acid monohydrate (25.9 g, 136.5 mmol). The mixture was stirred at room temperature for 10 h. The title compound was collected by filtration (69.3 g, 92%), mp>200° C. $^1$H NMR (400 MHz, (D$_3$C)$_2$SO) δ 10.44 (s, 1H, ArNH), 8.30 (bs, 2H, NH$_2$), 7.71 (d, J=1.6 Hz, 2H, ArH), 7.51 (ABq, J=6.4 Hz, 2H, ArH), 7.37 (t, J=1.6 Hz, 1H, ArH), 7.30 (ABq, J=7.4 Hz, 2H, ArH), 7.28 (ABq, J=7.4 Hz, 2H, ArH), 7.11 (ABq, J=6.4 Hz, 2H, ArH), 3.40 (ABq, J=14.0, 1H. ArCH$_2$), 3.20 (ABq, J=14.0 Hz, ArCH$_2$), 2.27 (s, 3H, CH$_3$), 2.27 (s, 3H, CH$_3$), 1.66 (s, 3H, CH$_3$); MS: m/z 406 (M$^+$); Anal. calcd for C$_{24}$H$_{23}$Cl$_2$F$_3$N$_2$O$_5$S: C, 49.75; H, 4.00; Cl, 12.24; N, 4.88. Found: C, 49.87; H, 3.99; Cl, 12.40; N, 4.84.

We claim:

1. A process for preparing a compound of formula I:

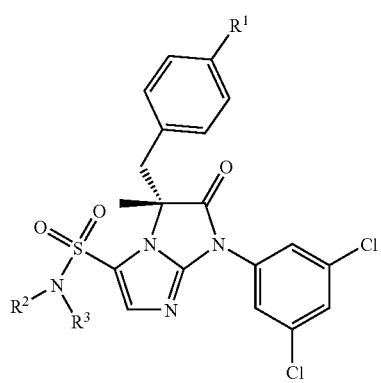

wherein

R$^1$ is selected from bromo, trifluoromethoxy, cyano and pyrimidin-5-yl optionally mono- or di-subsituted by NH$_2$; and R$^2$ and R$^3$ are each independently selected from the group consisting of
  (A) hydrogen; and
  (B) a C$_{1-4}$ straight or branched alkyl group, optionally mono- or disubstituted with moieties independently selected from oxo, —OH, NH$_2$ and —C(O)NR$^4$R$^5$, where R$^4$ and R$^5$ are independently selected from:
    (1) hydrogen, and
    (2) a C$_{1-4}$ straight or branched alkyl group which alkyl group is mono- or disubstituted with moieties independently selected from CONH$_2$ and OH;

or

R$^2$ and R$^3$, combined with the nitrogen they are bonded to, form:
  (1) a pyrrolidine or piperidine ring, each optionally substituted with the group —C(O)NR$^6$R$^7$, where R$^6$ and R$^7$ are independently selected from
    (A) hydrogen; and
    (B) a C$_{1-4}$ straight or branched alkyl group, optionally mono- or disubstituted with moieties independently selected from oxo, —OH and NH$_2$;
  (2) a morpholine ring; or
  (3) a piperazine ring;

or a pharmaceutically acceptable salt thereof;

said process comprising the step of reacting a compound of formula XXII with a compound of formula R$^d$MgY, where R$^d$ is C$_{1-6}$ alkyl or C$_{3-6}$cycloalkyl and Y is halogen, sulfur dioxide and N-chlorosuccinimide, followed by a base and a compound of the formula XXIII in an aprotic organic solvent to form a compound of the formula I, without isolation of intermediates formed during this step:

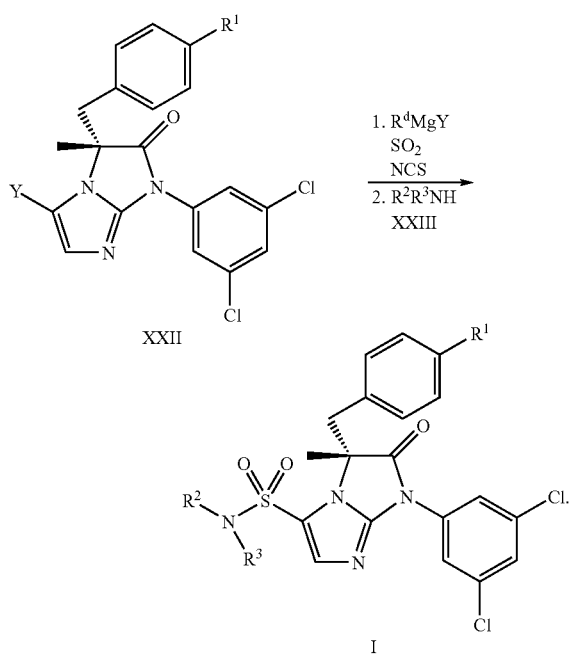

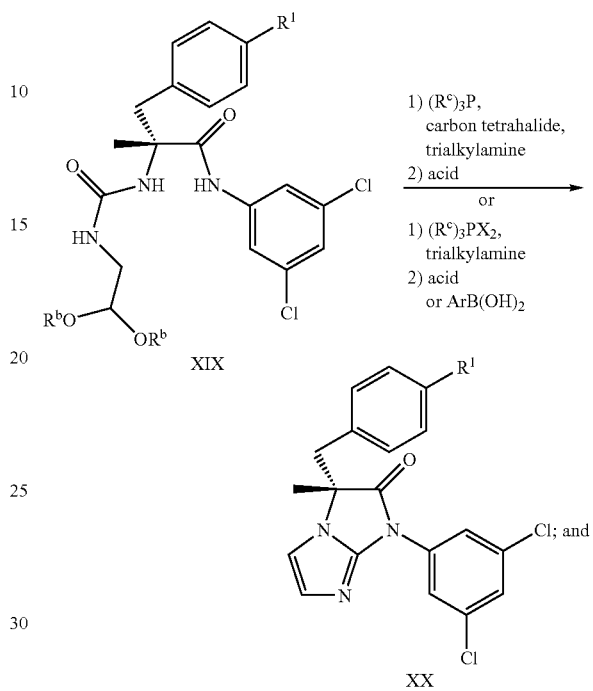

2. A process according to claim 1, wherein:
$R^1$ is selected from bromo, trifluoromethoxy, cyano and pyrimidin-5-yl;
$R^2$ is H; and
$R^3$ is —CH($R^8$)C(O)NH$_2$, where $R^8$ is a straight or branched $C_{1-3}$alkyl group; or
$R^2$ and $R^3$, together with the nitrogen they are bonded to form a moiety selected from

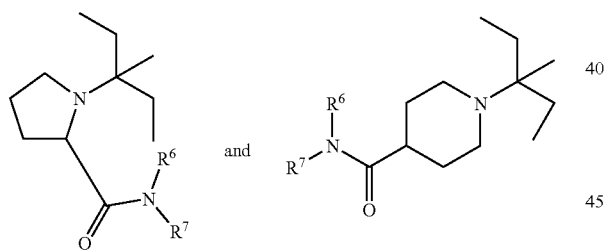

where $R^6$ and $R^7$ are independently selected from H and straight or branched $C_{1-4}$alkyl optionally substituted with OH.

3. A process according to claim 1, wherein the compound of formula XXII is prepared by a process comprising the steps of:
a) reacting the compound of formula XIX, wherein $R^1$ is as defined in claim 1 and $R^b$ is $C_{1-4}$ alkyl, with a compound of formula $(R^c)_3P$, where $R^c$ is $C_{1-4}$alkyl, $C_{3-6}$cycloalkyl or aryl, a carbon tetrahalide and a tri-$C_{1-6}$alkylamine in an aprotic organic solvent, followed by adding an acid to form a compound of the formula XX, or
a) alternatively, reacting a compound of the formula XIX, wherein $R^1$ is as defined in claim 1 and $R^b$ is $C_{1-4}$ alkyl, with a compound of the formula $(R^c)_3PX_2$, wherein $R^c$ is $C_{1-4}$alkyl, $C_{3-6}$cycloalkyl or aryl, and X is a halide, and a tri-$C_{1-6}$alkylamine, in an aprotic organic solvent, followed by adding an acid to form a compound of the formula XX, or a) alternatively, reacting a compound of formula XIX with a boronic acid compound ArB(OH)$_2$, wherein Ar is an aromatic carbocyclic group substituted with one or more electron withdrawing groups, in an aprotic organic solvent to form a compound of the formula XX:

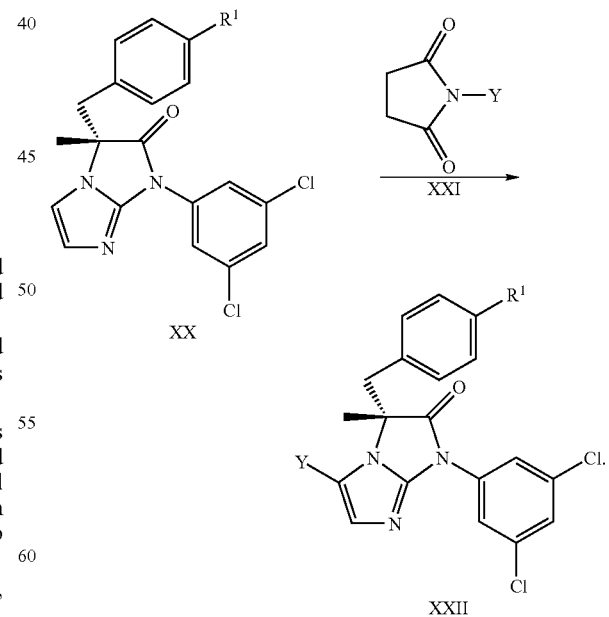

b) reacting the compound of the formula XX produced in step a) with a compound of the formula XXI, where Y is a halogen, in a aprotic organic solvent to form a compound of the formula XXII:

4. A process according to claim 3, wherein the compound of formula XIX is prepared by a process comprising reacting the compound of formula XVII, where $R^1$ is as defined in claim 3, with a compound of formula XVIII, where $R^a$ is aryl and $R^b$ is $C_{1-4}$ alkyl, and an organic base in a polar organic solvent to form a compound of the formula XIX:
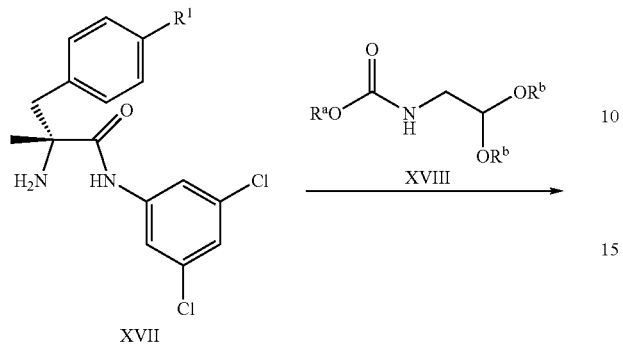
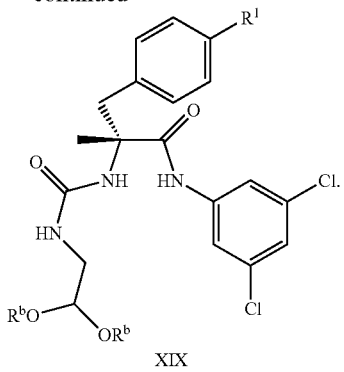
* * * * *